(12) United States Patent
Waters

(10) Patent No.: US 7,695,406 B2
(45) Date of Patent: Apr. 13, 2010

(54) USER INTERACTIVE EXERCISE SYSTEM

(76) Inventor: Rolland M. Waters, 1803 180th Ave. NE., Bellevue, WA (US) 98008

( * ) Notice: Subject to any disclaimer, the term of this patent is extended or adjusted under 35 U.S.C. 154(b) by 1402 days.

(21) Appl. No.: 11/078,913

(22) Filed: Mar. 9, 2005

(65) Prior Publication Data

US 2006/0229163 A1      Oct. 12, 2006

Related U.S. Application Data

(60) Provisional application No. 60/551,366, filed on Mar. 9, 2004.

(51) Int. Cl.
*A63B 71/00* (2006.01)

(52) U.S. Cl. .......................................................... 482/8

(58) Field of Classification Search ...................... 482/1, 482/4, 5, 6, 7, 8, 9, 51, 57, 900, 901, 902, 482/2, 3; 601/23, 33, 35, 36; 434/247; 463/1; 715/700, 706, 719; 700/91, 92
See application file for complete search history.

(56) References Cited

U.S. PATENT DOCUMENTS 5,213,555 A  *  5/1993  Hood et al. .................... 482/57
5,516,105 A      5/1996  Eisenbrey et al.
5,890,995 A      4/1999  Bobick et al.
5,955,667 A      9/1999  Fyfe
6,152,856 A  * 11/2000  Studor et al. ................... 482/8
6,244,988 B1 *  6/2001  Delman .......................... 482/8
6,301,964 B1   10/2001  Fyfe et al.
6,447,424 B1    9/2002  Ashby et al.
6,513,381 B2    2/2003  Fyfe et al.
6,902,513 B1 *  6/2005  McClure ......................... 482/8
7,128,693 B2 * 10/2006  Brown et al. ................... 482/8
7,556,590 B2 *  7/2009  Watterson et al. .............. 482/8
2002/0045519 A1*  4/2002  Watterson et al. ............. 482/54
2005/0239601 A1* 10/2005  Thomas ......................... 482/1
2006/0205569 A1*  9/2006  Watterson et al. ............. 482/54

* cited by examiner

*Primary Examiner*—Loan H Thanh
*Assistant Examiner*—Tam Nguyen
(74) *Attorney, Agent, or Firm*—Black Lowe & Graham PLLC; P. G. Scott Born

(57) ABSTRACT

System and method for interactive video game fitness equipment. Fitness hardware (e.g., an exercise bicycle, a stair machine, treadmill, elliptical trainer, rotary climbing wall, or other fitness equipment) interacts with a video game, optionally via various devices, e.g., a PC, gaming console, or other hardware and/or software device or system capable of implementing an interactive application), for an immersive hybrid exercise/game user experience.

2 Claims, 19 Drawing Sheets

| MARKET PLAYERS | STANDARD INTERFACE WITH 3RD PARTY CONTENT? | MASS-MARKET OR ELITE? | USERS CAN COMPETE HEAD-HEAD? | INTEGRATES WITH VCR-DVD & CD-MP3? | INTEGRATES WITH PC OR CONSOLES? | # OF BRANDS SUPPORTING INTERFACE |
|---|---|---|---|---|---|---|
| A | NO | ELITE | NO | NO | NO | 1 |
| B | NO | ELITE | NO | NO | NO | 1 |
| HEARTRATE | YES | BOTH | YES | YES | BOTH | ALL |
| D | NO | BOTH | NO | YES | NO | 4 |
| E | SOME | ELITE | YES | NO | PC-ONLY | 1 |
| F | NO | ELITE | YES | NO | PC-ONLY | 1 |

| | IEXERCISE | OTHERS |
|---|---|---|
| CONTROLS EXERCISE EQUIPMENT | YES | YES |
| WORKS WITH WORKOUT MUSIC & VIDEOS | YES | YES |
| ALLOWS AUTOMATIC UPLOAD OF EXERCISE DATA | YES | NO |
| ENABLES TRUE INTERACTIVE GAMES | YES | NO |
| ALLOWS USERS TO COMPETE HEAD-TO-HEAD | YES | NO |
| CONNECTS TO PCS & GAME CONSOLES | YES | NO |
| AVAILABLE TO ALL BRANDS OF EQUIPMENT | YES | NO |

FIG.19

USER INTERACTIVE EXERCISE SYSTEM

PRIORITY CLAIM

This application claims priority to U.S. Provisional Application Ser. No. 60/551,366 filed Mar. 9, 2004, incorporated by reference in its entirety herein.

COPYRIGHT NOTICE

This disclosure is protected under United States and International Copyright Laws. © 2002-2005 HeartRate Games, Inc. All Rights Reserved. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates generally to computer and video game technology and, more specifically, to video games played with and/or through fitness equipment.

BACKGROUND OF THE INVENTION

Currently people are forced to exercise indoors on fitness equipment without any interactivity, resulting in a boring experience that requires significant willpower to start and continue, resulting in considerable lack of motivation to keeping in shape, much less form healthy exercise habits. In the preferred embodiment the problem is solved by turning exercising on a piece of fitness equipment into an interactive, exciting, and motivating video game experience.

Another existing problem is active or fitness games have yet to penetrate the home in any significant degree; while an arcade game can be successful enough to support a proprietary solution, no single game, or even small set of games, is sufficient to motivate the consumer to make a substantial hardware purchase. Industry-wide support must be shown before most consumers will adopt a platform.

The current market solutions are inadequate. Proprietary solutions generally target niche markets and may consist of a proprietary hardware device, such as a bicycle or treadmill, an interface, and some proprietary software that runs the application; the user is require to supply the platform, usually a personal computer (PC). These solutions are closed, meaning there is absolutely no support for their devices other than from a few choice partners, and their costs force pricing high far above the mass-market.

Other approaches rely on the use of existing games that do not work off-the-shelf as fitness games. Further, because the devices do not provide a way to equally compare the effort put forth by two competitors, these devices can't be used for head-to-head competition or even friendly training.

In prior devices, there is no feedback from the device, so they cannot be used for interactive games or competitive events, and the settings of speed and incline or resistance are absolute, not relative, which means that a given workout is only good for someone within a narrow fitness range. Someone more fit than that range will find the workout too easy; for someone less fit the workout is too hard.

The preferred embodiment is based in part on two observations: most people find aerobic exercise boring and active games are very popular in arcades.

SUMMARY OF THE INVENTION

The preferred embodiment describes generic interactive fitness equipment using a rear-wheel trainer used with a bicycle interfaced to a personal computer (PC). The fitness equipment interaction happens in concert between the fitness hardware and a host device, e.g., a PC, game console, or other hardware and/or software device or system capable of implementing an interactive application.

Alternative embodiments include an exercise bicycle, a stair machine, treadmill, elliptical trainer, rotary climbing wall, or other fitness equipment, whether common or esoteric.

BRIEF DESCRIPTION OF THE DRAWINGS

Preferred and alternative embodiments of the present invention are described in detail below with reference to the following drawings.

FIG. 13 shows internal design which optionally allows multiple device types to be integrated and made equivalent in an equivalence layer, while simultaneously preserving device specific information in exercise records and elsewhere to meet the user's needs and for future expansion.

FIG. 18 compares products and features;

FIG. 19 shows advantages of a preferred embodiment and;

DETAILED DESCRIPTION OF THE PREFERRED EMBODIMENT

Figure 1:
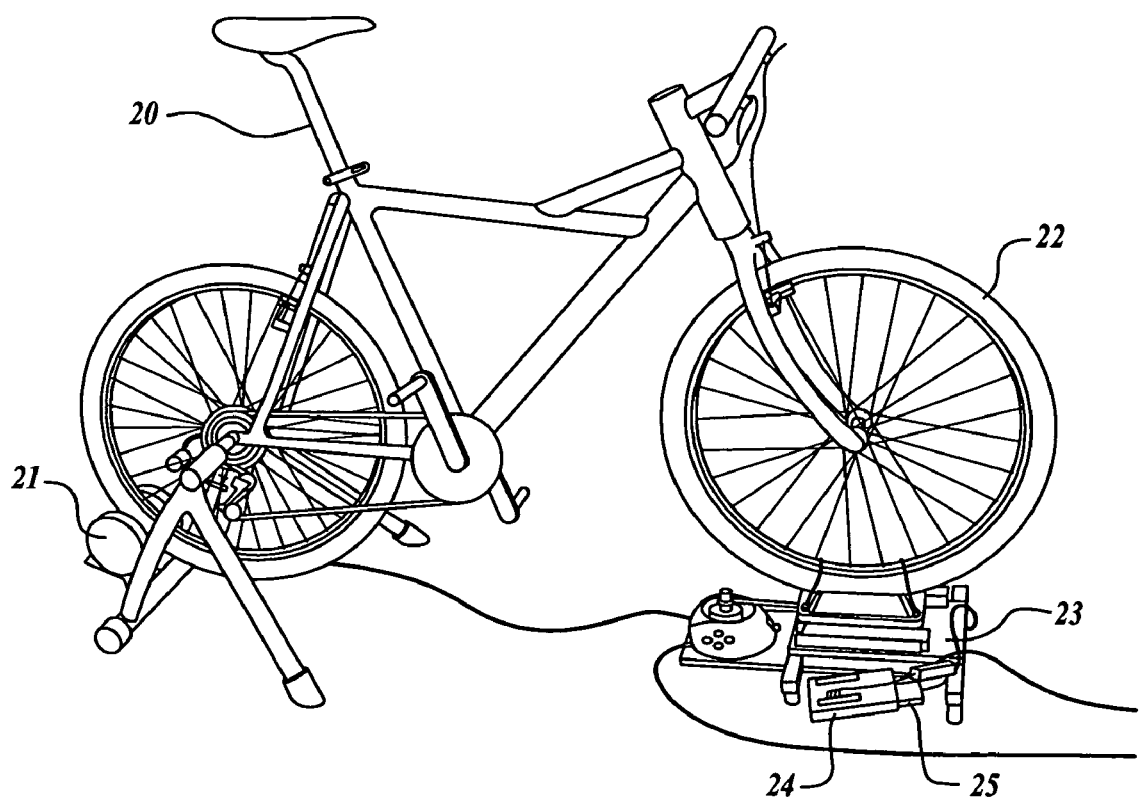
FIG. 1 is a conventional bicycle installed in rear-wheel trainer.

The preferred embodiment comprises one or more of the following: a fitness device (aka fitness machine, e.g., treadmill, stationary bicycle); a user display; a computer system for running a game (simulation or other software, e.g., PC, game console, or handheld device). Alternate embodiments may also include a method of detecting the level of effort of the user (e.g., momentary watts of output); and/or an optional method for monitoring the user (e.g., their perceived level of exertion).

The preferred embodiment can provide an interface that allows any fitness machine to look like a single-axis joystick. In an alternative embodiment multiple additional axes are possible (e.g., steering on a bicycle). The preferred embodiment may include buttons and sliders which may be reported out to common USB Human Interface Device (HID) spec drivers. The preferred embodiment may have connectivity with a PC, Xbox, PS2, Game Cube, etc. In an alternative embodiment two-way control (e.g., force feedback, increased device speed or resistance) will be available as well.

The preferred embodiment includes an interface that allows control of any fitness machine from an Application Programmer's Interface (API) which may run on top of a manufacturer's published or non-published interfaces. Examples of such interfaces: Icon's iFit interface (e.g., chirpmaker code); and Precor et al.'s CSafe interface (e.g., HRG code); direct control of a machine using the equivalent of the LabJack USB controls for our Torcs demo (e.g. HRG code, LabJack USB driver code and hardware). All code mentioned in this paragraph is herein incorporated by reference.

In the preferred embodiment the code resides on the device itself, in an interface pod, or on any other part or combination of parts of the fitness solution, including any main CPU.

The preferred embodiment optionally includes a calibration of level of effort between machines: of a single type, e.g., two machines of the same type from the same manufacturer; of same type but different manufacturers, e.g., two different stationary bicycles; and of different type and classes, e.g., a stationary bicycle and a treadmill. Equivalence between users on the same machine, or on machines made equivalent through the use of this interface allows a "fair fight" no matter what the two machines are, thus allowing for multi-person sessions locally or over a network.

The preferred embodiment allows automatic adjustment to machine settings, including level of effort. First, for an experienced user on a new machine e.g., doesn't have to know how to setup a machine he or she hasn't used before because the system knows specific characteristics of the user and can compute the appropriate settings. Second, between a user and a user's exercise plan; the interface knows sufficient data about the exercise plan and the level of effort. Third, for a naïve user, who needs their fitness level evaluated the system can automatically adjust to an appropriate baseline based on data from one or more sessions. Finally for a user against AI or other elements of a game or other simulation system, adjusting the user's capabilities to a known baseline appropriate for a designer's desired level of difficulty.

In a preferred embodiment, code implementing the settings feature is provided below:

```
[multiplayer]
server_ip="192.168.0.155"
server_port=8000
multiplayer_on=0
hrg_mode_on=1
my_car_index=0
my_car_name="Player CLK DTM"
use_pos=1
use_accel_brake_steer=0
collision_on=1
num_players=2
bike_max_speed_param = 80.0
bike_speed_factor_param = 2.1
car_send_interval_msecs_param = 33.0
HRG_EASIER_SPEED_BUTTON=4
HRG_HARDER_SPEED_BUTTON=5
HRG_RESET_SPEED_BUTTON=6
HRG_REVERSE_BUTTON=1
HRG_FORWARD_BUTTON=3
[pace]
HRG_MAX_PACE=30.0
/* trainer 0 = minoura */
[trainer0]
trainer_speed_factor = 1.0
/* trainer 1 = cyclops */
[trainer1]
trainer_speed_factor = 1.6
/* trainer 7 = minoura mag 850 high setting*/
[trainer7]
trainer_speed_factor = 0.7
[berniw0]
max_speed=90.0
[berniw1]
max_speed=92.0
[berniw2]
max_speed=94.0
[berniw3]
max_speed=96.0
[berniw4]
max_speed=98.0
[berniw5]
max_speed=91.0
[berniw6]
max_speed=93.0
[berniw7]
max_speed=95.0
[berniw8]
max_speed=97.0
[berniw9]
max_speed=99.0
[user]
first_name="johnny"
middle_name = "a"
last_name = "fernandes"
dob_m = 1
dob_d = 31
dob_y = 1966
sex = 1
weight_lbs = 180
height_ft = 5.6
target_heart_rate = 60
fitness_level = 1
performance_level = 100
physician_supervision = 0
[recording]
directory = "./hrg_data_dump"
file_prefix = "testjf"
writing_on = 1
writing_interval_secs = 30
```

In the preferred embodiment the traditional AI balance technique of "Rubberbanding" is not preferred. Unlike in a traditional game, where "throttle is free", i.e., it costs the user no effort to hold the throttle wide open for long periods of time, for an exercise game or simulation to be "fair" and "beatable" the system needs to know the actual potential of the user and the system. For example, a typical car racing game would speed up the AI cars the user is racing against when the user is going fast, allowing them to catch up, and slow them down somewhat when the user is behind, mounting the cars on a "rubber band" relative to the user's car. Since there is no "cost" to the user to go as fast as possible this is a reasonable technique in a standard game. However, if an exercise system were to implement such a simple system, the users would quickly learn that they should go as slow as possible for the majority of the race, speeding up only near the end. This would result in an exercise system that was neither a fun nor effective. Instead, the system is designed to be able to change the dynamics of the "fitness solution" relative to the characteristics of each individual exerciser. In order to accomplish this task the system acquires knowledge of the user, and/or a good muscle/skeletal model of human output that understands quickly the individual's ability. The preferred embodiment executes an example of this process by using code in hrg_speed_limiter.cpp which works by modeling physical dynamics of an actual machine, e.g., power/RPM curve of a bicycle trainer, using a straight watts equivalent, to control the maximum speed of the AI cars along with their aggressive or passive nature (e.g., for passing), based on how well or poorly the user is doing. Alternative embodiments may use programming models including: Bicycle (power/speed) or Treadmill/Walking (speed/incline/weight).

Code implementing a preferred speed limiter feature is provided below:

```
#include <direct.h>
#include "pace.h"
#ifdef DMALLOC
#include "dmalloc.h"
#endif
#define HRG_SP_RE_IMPORT
#include "car.h"
extern MyCar* mycar[ ];
float getHRGSpeedLimiter( int index, MyCar* myc, char *nameStr)
    {
    // decide how we want to drive --- HRG method
    //MyCar* myc = mycar[index-1];
    float metersAhead = g_race_distances[ index] - g_player_race_distance;
    float speedLimiter = 1.0f; // limit our acceleration
    static int lastType[ 40] = {myc->INSANE};
    static float VERY_SLOW_DISTANCE = 450.0f;
    static float SLOW_DISTANCE = 300.0f;
    static float CAREFUL_DISTANCE = 150.0f;
    static float NORMAL_DISTANCE = -30.0f;
    static float PUSH_DISTANCE = -200.0f;
    //static float INSANE_DISTANCE = -300.0f; // not used
    static float VERY_SLOW_LIMITER = 0.4f;
    static float SLOW_LIMITER = 0.6f;
    static float CAREFUL_LIMITER = 0.7f;
    static float NORMAL_LIMITER = 0.8f;
    static float PUSH_LIMITER = 0.9f;
    static float INSANE_LIMITER = 1.0f;
    // for now, the types seem to give mostly aberrant behavior, so we
    // won't tweak them much.
    #define VERY_SLOW_TYPE      myc->CAREFUL    // slow type means they just basically don't pass
    #define SLOW_TYPE           myc->CAREFUL
    #define CAREFUL_TYPE        myc->NORMAL
    #define NORMAL_TYPE         myc->NORMAL
    #define PUSH_TYPE           myc->PUSH
    #define INSANE_TYPE         myc->PUSH       // insane type is _really_ crazy
    if (metersAhead > VERY_SLOW_DISTANCE)
        {
        myc->loadBehaviour( VERY_SLOW_TYPE); //note that behavior support goes no slower than "slow"
        speedLimiter = VERY_SLOW_LIMITER; // but we can still throttle the guy way way back
        if (lastType[ index] != VERY_SLOW_TYPE)
            {
            //GfOut( "%s (%d): ahead by %.1f; new behavior is %s; limiter is %.2f\n", nameStr, index,
metersAhead, "SLOW", speedLimiter);
            lastType[ index] = VERY_SLOW_TYPE;
            }
        }
    if (metersAhead > SLOW_DISTANCE)
        {
        myc->loadBehaviour( SLOW_TYPE);
        speedLimiter = SLOW_LIMITER;
        if (lastType[ index] != SLOW_TYPE)
            {
            //GfOut( "%s (%d): ahead by %.1f; new behavior is %s; limiter is %.2f\n", nameStr, index,
metersAhead, "SLOW", speedLimiter);
            lastType[ index] = SLOW_TYPE;
            }
        }
        else if (metersAhead > CAREFUL_DISTANCE)
        {
        myc->loadBehaviour( CAREFUL_TYPE);
        speedLimiter = CAREFUL_LIMITER;
        if (lastType[ index] != CAREFUL_TYPE)
```

```
        {
            //GfOut( "%s (%d): ahead by %.1f; new behavior is %s; limiter is %.2f\n", nameStr, index,
metersAhead, "CAREFUL", speedLimiter);
            lastType[ index] = CAREFUL_TYPE;
        }
    }
    else if (metersAhead > NORMAL_DISTANCE)
    {
        myc->loadBehaviour( NORMAL_TYPE);
        speedLimiter = NORMAL_LIMITER;
        if (lastType[ index] != NORMAL_TYPE)
        {
            //GfOut( "%s (%d): ahead by %.1f; new behavior is %s; limiter is %.2f\n", nameStr, index,
metersAhead, "NORMAL", speedLimiter);
            lastType[ index] = NORMAL_TYPE;
        }
    }
    else if (metersAhead > PUSH_DISTANCE)
    {
        myc->loadBehaviour( PUSH_TYPE);
        speedLimiter = PUSH_LIMITER;
        if (lastType[ index] != PUSH_TYPE)
        {
            //GfOut( "%s (%d): ahead by %.1f; new behavior is %s; limiter is %.2f\n", nameStr, index,
metersAhead, "PUSH", speedLimiter);
            lastType[ index] = PUSH_TYPE;
        }
    }
    else
    {
        myc->loadBehaviour( INSANE_TYPE);
        speedLimiter = INSANE_LIMITER;
        if (lastType[ index] != INSANE_TYPE)
        {
            //GfOut( "%s (%d): ahead by %.1f; new behavior is %s; limiter is %.2f\n", nameStr, index,
metersAhead, "INSANE", speedLimiter);
            lastType[ index] = INSANE_TYPE;
        }
    }
    return( speedLimiter);}
```

Preferably, there is additional level of input massaging: braking (an additional joystick axis) generated automatically by processing the "input signal" from the rotation of the rear wheel or equivalent energy absorption/storage/dissipater device as demonstrated demo with bicycle on standard rear-wheel trainer. Braking is preferably included because in order for a more realistic and engaging experience the user should be able to slow down as well as speed up.

Preferably, input from human is modeled from knowledge of the mechanical nature of the human body in one or more of the following ways: baseline (D/C) offset plus A/C signal (treating both legs as one input), baseline (D/C) offset plus two A/C signals (treating each leg separately), two A/C signals (treating legs either together or separately).

Alternatively, additional models are derivable for all types of fitness machines (e.g., rowing, elliptical trainers, treadmills, etc.), based on knowing or assuming the power characteristics of the dissipative device (typically exponential with respect to the current short-term average input power for the human).

The preferred embodiment can also detect changes in output energy (e.g., constant, increases, or decays, or decays rapidly) and thereby can distinguish or separate: acceleration by user, braking with hand brake on rear wheel, and coasting steady-state pedaling/running/rowing/etc.

In a preferred embodiment, code implementing the brake detection feature is provided below:

```
#define        HRG_EASIER_SPEED_KEY        'J'
#define        HRG_HARDER_SPEED_KEY        'K'
#define        HRG_RESET_SPEED_KEY         'L'
#define        HRG_REVERSE_KEY             'R'
#define        HRG_FORWARD_KEY             'F'
//#define      HRG_EASIER_SPEED_BUTTON4
//#define      HRG_HARDER_SPEED_BUTTON 5
//#define      HRG_RESET_SPEED_BUTTON 6
//#define      HRG_REVERSE_BUTTON 1
//#define      HRG_FORWARD_BUTTON 3
long    gHRG_EASIER_SPEED_BUTTON =4;
long    gHRG_HARDER_SPEED_BUTTON= 5;
long    gHRG_RESET_SPEED_BUTTON= 6;
long    gHRG_REVERSE_BUTTON =1;
```

```
long     gHRG_FORWARD_BUTTON =3;
unsigned char turn_on_debug=0;
unsigned char g_trainer_type = 0;
float g_trainer_speed_factor= 1.0;
static unsigned char     g_hrg_forward = 1;
  float           g_hrg_bike_max_speed;
  long g_last_send_time = 0;
#define JIFH(x) if ( (x) != 1 ) \
     {GfOut("**** HRG Failed in %s rc=%d\n",#x,x);}
#define SPEED_HIST_SIZE50           // how many samples to keep for average
float g_speed_samples[SPEED_HIST_SIZE];
typedef struct
{
   float speed;
   unsigned char braking_on;
   float braking_amount;
} BIKE_INFO;
BIKE_INFO g_bike_info;
int AddValToSpeedArray(float val)
   unsigned long i;
   for(i=0; i < (SPEED_HIST_SIZE - 1); i++)
   { g_speed_samples[i] = g_speed_samples[i+1];
   }
   g_speed_samples[SPEED_HIST_SIZE - 1] = val;
   return 1;
}
int GetSpeedAverage( unsigned long sample_size,
              float *p_average)
{
   unsigned long i;
   float total = 0;
   if(! p_average)
   { GfOut("Error1 in Human.cpp:GetSpeedAverage\n");
       return 0;
   }
   if((sample_size > SPEED_HIST_SIZE) || (sample_size == 0))
   {
       GfOut("Error2 in Human.cpp:GetSpeedAverage\n");
       return 0;
   }
   total = 0;
   for(i=SPEED_HIST_SIZE; i > (SPEED_HIST_SIZE - sample_size); i--)
   {
       total += g_speed_samples[i-1];
   }
   *p_average = total / ((float) sample_size);
   return 1;
}
#define SHOW_RAW_VALUES 0
int GetBikeSpeedNew(float *p_speed,
              unsigned char *p_braking_on,
              float *p_braking_amount)
{
   float val_to_graph;
   //char str[256];
   double count,elapsed_millisecs;
   if((! p_speed) || (! p_braking_on) || (! p_braking_amount))
   {
       GfOut("GetBikeSpeedNew: ERROR Invalid params\n");
       return 0;
   }
   if(! hrg_LJ_GetCount(&count, &elapsed_millisecs))
   {
        GfOut("GetBikeSpeedNew: ERROR getting count\n");
        return 0;
   }
       static int brake_detect_val = 0;
       static float brakeThreshold = 1.2f; // might want to play with this one more
       static bool was_braking = false;
       static int min_braking = -2;
       static int max_braking = 12;
       static int braking_threshold = 1; // 2 might get touch fewer false positives, but hurts latency
       static int high_braking_threshold = 6; // if above this, we do a different check to see if braking
       float avg_speed;
       float last_avg_speed = 0;
       static int num_samples_to_average = 4; // three works good too!
       float sampled_average = 0.0f;
       float last_sampled_average = 0.0f;
       static int num_samples_in_short_average = 7; // was 15, we need to understand this better
```

```
    float short_avg_speed = 0.0f;
    static float BrakePressureStartVal = 0.4f; // scale of 0.000 to 1.0
    static float BrakePressureIncrement = 0.1f; // same scale
    static float BrakePressureIncrementThreshold = 1.3f; // percentage, see code below
    static int BrakePressureMaxIncrements = 6;
    float brake_pressure = 0.0f;
    static float brake_pressure_last = 0.0f;
    GetSpeedAverage( num_samples_to_average, &last_sampled_average);
    GetSpeedAverage( SPEED_HIST_SIZE, &last_avg_speed);
    float this_speed = (float) ((float) count * 100.0) / (float) elapsed_millisecs;
    AddValToSpeedArray( this_speed);
    GetSpeedAverage( SPEED_HIST_SIZE, &avg_speed);
    GetSpeedAverage( num_samples_to_average, &sampled_average);
    GetSpeedAverage( num_samples_in_short_average, &short_avg_speed);
    val_to_graph = avg_speed;
    // if we're braking by any measure, up the brake detection value
    //if ((sampled_average * brakeThreshold < short_avg_speed ) && (avg_speed < last_avg_speed)
&& (sampled_average < last_sampled_average))// && (this_speed < )
    if ((this_speed * brakeThreshold < short_avg_speed ) && ((short_avg_speed * (1.0f +
brakeThreshold) / 2) < last_avg_speed) && (avg_speed < last_avg_speed) && (sampled_average <
last_sampled_average))// && (this_speed < )
    {
       brake_detect_val += 1;
    }
    else if ((brake_detect_val > high_braking_threshold) || (this_speed < 0.001) || (short_avg_speed <
0.001)) // if we have been braking for a while, keep braking longer
       {
         if ((short_avg_speed < last_avg_speed) || (this_speed < 0.001) || (short_avg_speed < 0.001))
            {
            brake_detect_val += 1; // still braking
            }
            else
            {
            brake_detect_val -= 1; // start getting off the brakes
            }
       }
    else
    {
       brake_detect_val -= 1; // get off the brakes, at least a bit.
    }
    // keep the brake detection value within reasonable bounds
    {
       brake_detect_val = (brake_detect_val <= min_braking) ? min_braking : (brake_detect_val);
       brake_detect_val = (brake_detect_val >= max_braking) ? max_braking : (brake_detect_val);
    }
    if (brake_detect_val >= braking_threshold)
    {
            brake_pressure = BrakePressureStartVal;
            float brakeCalc1 = this_speed * brakeThreshold;
       float brakeCalc2 = short_avg_speed * (1.0f + brakeThreshold) / 2;
            int numIncrements = 0;
            for (numIncrements = 0; numIncrements < BrakePressureMaxIncrements;
numIncrements++)
            {
          brakeCalc1 *= BrakePressureIncrementThreshold;
          brakeCalc2 *= (1 + BrakePressureIncrementThreshold) / 2;
               if ((brakeCalc1 < short_avg_speed) && (brakeCalc2 < last_avg_speed))
               {
                  brake_pressure += BrakePressureIncrement;
               }
               else
                  break;
            }
       if (!was_braking)
       {
            was_braking = true;
            //brake_detect_val += 3; // once the brakes are on, keep them on for a bit
       }
       else
       {
            if ((this_speed < 0.001) || (short_avg_speed < 0.001))
            {
             // and if they're almost stopped, we don't back off at all
               brake_pressure = (brake_pressure_last > brake_pressure) ? (brake_pressure_last) :
brake_pressure;
            }
            else // we let them brake harder by an increment but only back of a bit at a time
            {
            if (brake_pressure_last > brake_pressure)
```

```
          {
            brake_pressure = brake_pressure_last − (BrakePressureIncrement / 2);
          }
          else if (brake_pressure_last < brake_pressure)
          {
            brake_pressure = brake_pressure_last + BrakePressureIncrement;
          }
        }
      }
      //Graph.SetColorEZ( (int) (255*(brake_pressure)), (int) (255*(brake_pressure))); // color as
braking (darkish blue tending to white)
      //TRACE("brake pressure = %.1f ", brake_pressure);
        }
        else
        {
          was_braking = false;
          brake_pressure = 0.0;
     //    Graph.SetColorEZ( 0, 0); // color as normal
        }
        //sprintf(str, "speed: this = %3.1f sampled = %3.1f lastS = %3.1f avg = %3.1f lastA = %3.1f
msecs = %5.1f brake: %s count %d\n", this_speed, sampled_average, last_sampled_average, avg_speed,
last_avg_speed, elapsed_millisecs, ((brake_detect_val > braking_threshold) ? "yes" : "no "), brake_detect_val);
        brake_pressure_last = brake_pressure; // save it for later
        *p_braking_on = was_braking;
        *p_braking_amount = brake_pressure;
        *p_speed = val_to_graph;
      //if(was_braking)
      //{
      //   GfOut("Braking on speed = %5.5f Amount = %5.5f\n", val_to_graph,brake_pressure);
      //}
  return 1;
}
DWORD WINAPI LabjackThreadProc(void *p_bike_info)
{
   BIKE_INFO *p_info;
   p_info = (BIKE_INFO *) p_bike_info;
   while(1)
   {
      GetBikeSpeedNew(&p_info->speed,
              &p_info->braking_on,
              &p_info->braking_amount);
     //GfOut("this is in JfThreadProc: %s\n", (char *) p_init_param);
      Sleep(1);
   }
   return 1;
}
static int
onKeyAction(unsigned char key, int modifier, int state)
{
    currentKey[key] = state;
    switch(toupper(key))
     {
     case HRG_EASIER_SPEED_KEY:
        g_hrg_bike_max_speed −= g_hrg_bike_speed_factor_param ;
        if(g_hrg_bike_max_speed < 1.0)
        {
          g_hrg_bike_max_speed = 1.0;
        }
        GfOut("Easier - hrg throttle resistance = %3.3f\n", g_hrg_bike_max_speed /
g_hrg_bike_max_speed_param);
       break;
       case HRG_HARDER_SPEED_KEY:
          g_hrg_bike_max_speed += g_hrg_bike_speed_factor_param ;
        GfOut("Harder  -  hrg  throttle  resistance  =  %3.3f\n",  g_hrg_bike_max_speed  /
g_hrg_bike_max_speed_param);
       break;
       case HRG_RESET_SPEED_KEY:
          g_hrg_bike_max_speed = g_hrg_bike_max_speed_param ;
        GfOut("Reset  -  hrg  throttle  resistance  =  %3.3f\n",  g_hrg_bike_max_speed  /
g_hrg_bike_max_speed_param);
       break;
       case HRG_REVERSE_KEY:
          g_hrg_forward = 0;
          GfOut("HRG direction: reverse\n");
       break;
       case HRG_FORWARD_KEY:
          g_hrg_forward = 1;
          GfOut("HRG direction: forward\n");
       break;
```

```
            default:
                break;
        }
    return 0;
}
static int
onSKeyAction(int key, int modifier, int state)
{
    currentSKey[key] = state;
    return 0;
}
//static void remote_car_common_drive(int index, tCarElt* car, tSituation *s)
//{
//}
#define COLLISION_THRESHOLD      30    //counter max
#define MAX_REVERSE_TIME_MSECS 1600      // millisecs
#define NOT_GOING_ANYWHERE_SPEED    0.5
#define GET_ME_UNSTUCK_SPEED   25.0
static void common_drive(int index, tCarElt* car, tSituation *s)
{
    tdble slip;
    static float ABS = 1.0;
    static float AntiSlip = 1.0;
    static int lap = 0;
    float ax0;
    float brake;
    float throttle;
    float leftSteer;
    float rightSteer;
    int scrw, scrh, dummy;
    static int firstTime = 1;
    static float prevLeftSteer = 0.0;
    static float prevRightSteer = 0.0;
  long curr_time=0;
  float curr_speed=0;
  float hrg_brake=0;
  float hrg_accel=0;
   float hrg_throttle;
if((g_hrg_mode_on) && (strcmp(car->_name, g_hrg_my_car_name) == 0))
{
   if(joyInfo->levelup[gHRG_REVERSE_BUTTON])
       {
          g_hrg_forward = 0;
          GfOut("Direction: reverse\n"); }
     if(joyInfo->levelup[gHRG_FORWARD_BUTTON])
       {
          g_hrg_forward = 1;
          GfOut("Direction: forward\n");
          turn_on_debug = (turn_on_debug) ? 0 : 1;}
     if(joyInfo->levelup[gHRG_EASIER_SPEED_BUTTON])
       {
          g_hrg_bike_max_speed -= g_hrg_bike_speed_factor_param ;
          GfOut("Easier  -  hrg  throttle  resistance  =  %3.3f\n",  g_hrg_bike_max_speed  /
g_hrg_bike_max_speed_param);
       }
        if(joyInfo->levelup[gHRG_HARDER_SPEED_BUTTON])
       {
          g_hrg_bike_max_speed += g_hrg_bike_speed_factor_param ;
          GfOut("Harder  -  hrg  throttle  resistance  =  %3.3f\n",  g_hrg_bike_max_speed  /
g_hrg_bike_max_speed_param);
       }
     if(joyInfo->levelup[gHRG_RESET_SPEED_BUTTON])
       {
          g_hrg_bike_max_speed = g_hrg_bike_max_speed_param ;
          GfOut("Reset  -  hrg  throttle  resistance  =  %3.3f\n",  g_hrg_bike_max_speed  /
g_hrg_bike_max_speed_param );}
        unsigned char braking_on=0;
        float braking_amount;
         float sum_xy_speed=0;
        static int collision_count=0;
        static long reverse_start_time=0;
        curr_time = timeGetTime( );
        //the function GetBikeSpeedNew
         //
            curr_speed = g_bike_info.speed * g_trainer_speed_factor;
            braking_on = g_bike_info.braking_on;
            braking_amount = g_bike_info.braking_amount;
     sum_xy_speed = (fabs(car->_speed_X)) + (fabs(car->_speed_Y));
//if pedalling but car is not moving could mean a collision
```

-continued

```
// if this continues for a while, then we'll throw car in reverse
    if(g_hrg_forward)
    { //if( (curr_speed > GET_ME_UNSTUCK_SPEED) && (car->_gear >0) &&
        //((fabs(car->_speed_X) <= NOT_GOING_ANYWHERE_SPEED) ||
        //(fabs(car->_speed_Y) <= NOT_GOING_ANYWHERE_SPEED)) )
        if( (curr_speed > GET_ME_UNSTUCK_SPEED) && (car->_gear >0) &&
            (sum_xy_speed <= NOT_GOING_ANYWHERE_SPEED) )
        {
            collision_count++;
        }
        else
        {
            collision_count = 0;
        }
        if(collision_count > COLLISION_THRESHOLD)
        {
            g_hrg_forward = 0;
            collision_count = 0;
            reverse_start_time = curr_time;
        }
    }
    else
    {
        //only let car go in reverse for a short period
        if((curr_time - reverse_start_time) > MAX_REVERSE_TIME_MSECS)
        {
            g_hrg_forward = 1;
            collision_count = 0;
        }
    }
    if(curr_speed > g_hrg_bike_max_speed)
    {
        curr_speed = g_hrg_bike_max_speed;
    }
        if((curr_speed < 2.0) || (car->_gear == -1) || (sum_xy_speed < 0.5) )
        {
            braking_on = 0;
            braking_amount = 0.0;
        }
    if(g_hrg_forward)
    {
        hrg_throttle = (curr_speed) / (g_hrg_bike_max_speed) ;
        hrg_brake = 0.0;
        if(braking_on)
        {  //GfOut("Braking on?\n");
            hrg_brake = braking_amount;
            hrg_throttle = 0.0;
        }
    }
    else
    {
        hrg_brake = ((curr_speed) / (g_hrg_bike_max_speed)) * 1.5;
        hrg_throttle = 0.0;
    }
```

Alternative embodiments of inputs include total weight of user, and weight shifting left/right, front/back, or up/down unweighting and weighting which provide a increasingly realistic and meaningful experience to the user. An alternative embodiment may include detection of non-human input assists e.g., cheater detection.

The preferred embodiment includes a system that tracks the user and provides multiple levels of support: cross platform data reporting and analysis, understands exercise plans and provides guidance and control of the "fitness solution" about the user's needs for the current exercise session e.g., during the exercise session, notifies the "fitness solution" about: warm-up, cool down, and interval starts & ends. The preferred embodiment allows user to modify and store modifications to exercise plan either for this exercise session or the long-term plan, or both.

Another preferred embodiment allows the system to learn, through integrated or off-line analysis, the user's level of fitness which may be mediated/controlled by a coach, trainer, nurse, doctor or other professional. The preferred embodiment can provide automatic changes to exercise plans.

The preferred embodiment provides for finding "equals" or appropriate competitive/cooperative partners for multi-person fitness sessions that can be used to correlate a person's reported level of fitness through the interface to actual real-world fitness tests.

The preferred embodiment allows understanding of relative performance at in-person competitive events as compared to on-line and/or solo events. Preferably, the system can validate "real" users vs. cheaters.

An alternative embodiment allows extensions to the system, e.g., a RFID-encoded heart rate monitor, or the presence of an external device, such as card-key or cell phone, that allow users to be automatically identified to a fitness solution along with any other preferred or optional peripheral, such as body state monitors (e.g., heart rate, blood pressure, blood oxygen level, ECG/EKG, weight, body fat content, oxygen uptake, etc.)

The preferred embodiment will include sensors, actuators, etc., and their relevant interfaces which use any communication mechanism to the host, e.g., a wireless interface such as Bluetooth™, 802.11b, wireless USB, etc; a wired interface such as USB or Firewire™, etc; a fiber-optic interface; or any other interface capable of enabling communication between a sensor and the host.

The preferred embodiment consists of a software Application Programming Interface (API) and a USB-compliant hardware interface to fitness devices. This allows developers to create games for the PC, PS2, XBox, and other platforms and to use fitness equipment compliant with the preferred embodiment as easily as they would any other input device.

The preferred embodiment is designed for anybody who wants to be in better shape. Equipment enabled with the preferred embodiment changes the way people exercise: fun exercise that replaces boredom; and the ability to track and manage historical workout activity. For fitness equipment vendors, the preferred embodiment provides: product differentiation among other equipment OEMs and against existing products and drives replacement of existing equipment by existing customers. For workout and game publishers, the preferred embodiment enables a new interactive game platform: new life for existing workout video and music lines; and new life for existing games appropriate for exercise modalities. It provides a new game genre and market opportunity, interactive fitness games.

Because the preferred embodiment is provided by an independent company, preferably with expertise in middleware software, rather than a fitness equipment manufacturer or a proprietary game platform, it is far more likely to be received warmly rather than as a competitive threat.

The preferred embodiment is a benefit for consumers because the preferred embodiment represents a trusted interface brand, à la VHS tapes—they know that any IExercise[1]-labeled game will work with any IExercise-labeled fitness device, so they can shop for both games and devices without worrying about technical details. USB interfaces are provided on the Xbox, PlayStation2, and the PC, so consumers do not need to buy a new computer or game console.

[1] IExercise is a currently contemplated trademark for certain versions of the preferred embodiment. However, the scope of the invention is not to be limited by this trademark or any other.

In the preferred embodiment the cost of adding USB interface hardware to the exercise device is trivial, so price, configuration, and availability are not stumbling blocks for IExercise as they are for proprietary solutions. Consumers simply plug the USB cable from the device into their console or PC, insert the game disk and they are up and running.

The preferred embodiment has a broad game catalog which relates to market success of IExercise. Additionally, a selection of IExercise devices wide enough to appeal to most consumers would be available. The preferred embodiment reduces cost, especially of hardware implementation, maximizes market potential, minimizes time to market for products, minimizes development requirements for iExercise products, supports legacy & future hardware, and has no platform dependencies on the device side (i.e., all devices preferably work on all platforms, and/or maximize developer flexibility).

In the preferred embodiment both the elite and mass market are preferred customer bases. Elite users already consume devices, but the mass market will be the goal of most developers. Therefore, preferably, while the most critical features of the elite user should be implemented, the baseline criteria are ease of use, i.e., removal of stumbling blocks to adoption and continued use.

Preferably, the system is easy to use—for any game, with any device, the user can insert the game, plug in the device, and immediately begin playing without having to do any advanced configuration, e.g., log in, set up an exercise program, configure the device, etc. Preferably, reasonable defaults are provided for all configuration parameters.

In an alternative embodiment the following features will be added for advanced users: a calendar with exercise scheduling and reminders, results reporting and tracking, and training advice and help.

In the preferred embodiment several technical features have been distilled from the marketing requirements: Simplify development of fitness games, keep the developer from having to know about exercise physiology, applications and equipment must work on "first plug-in" without user intervention, ease of use is paramount. All of the above implies that fitness equipment should be more or less completely hidden from the user. This abstraction includes: device detail hiding, device equivalence e.g. any device can be used in place of any other, and user hiding e.g. while it is acceptable for the application to know about the user, the application must be able to run without any knowledge of the user.

In the preferred embodiment fitness equipment manufacturers are afforded as much flexibility in producing new hardware as game developers do software. This means that, in the preferred embodiment: any device can interface to IExercise USB hardware without driver changes, upgrades to devices must not require driver changes, and hardware interface requirements must not cause significant cost increases.

In the preferred embodiment users optionally have the following functionality available: scheduling exercise, reporting exercise results, tracking exercise results, enter the user information, e.g., weight and heart rate information, and allow for fitness testing.

In the preferred embodiment the API is built in several layers in order to achieve the following: offer maximum flexibility to developers by allowing them to choose the appropriate interface(s) for their application, create a dynamic system of extensible components that will accommodate future devices and application needs, allow modules to be designed, tested and updated independently.

In the preferred embodiment layers allow the interface to support all fitness equipment types, yet provide a simple programming model for the application. This allows rapid development of applications that automatically support all devices.

In the preferred embodiment it is anticipated that IExercise will appeal to a wide variety of developers with different skills, resources, and visions. There are the applications such as bike racing, virtual tours of cities, marathon training; a simple application on a cell phone or PDA to control the treadmill at the gym and record your workout, or a game of bike-powered Tetris are examples of more obscure uses.

The preferred embodiment employs a physics model that may be appropriate for any application that models "the real" world. It allows the application to set incline (slope), desired speed, and various types of resistance such as wind resistance and rolling (tire) resistance.

Another preferred embodiment employs an intensity model that may be appropriate for any application that just wants to make the player work harder at certain times than others. For instance, in a "Tetris" style falling blocks game, the game can increase the intensity near the end of a round. If the player walks, runs, or pedals faster than the intensity, then the rate of fall is slowed; otherwise it is increased.

Alternate embodiments employ a combination of "intensity" and "physics" and/or other models. In alternative embodiments, as new genres of applications arise and specific needs are identified, new interfaces will easily be added alongside the physics and intensity interfaces.

In the preferred embodiment, a device equivalence interface model is designed to allow an application to respond in a similar fashion across devices such as treadmills and bicycles. The mapping functionality provided in this interface can convert parameters from the various devices into a common unit such as power, thus providing an "equivalent" experience.

One embodiment includes a simple interface that provides functionality specific to a treadmill. Another embodiment includes a simple interface that provides functionality specific to bicycle.

In the preferred embodiment the generic device interface is the lowest layer in the architecture that may be useful for developers. As the foundation of the system, this interface was written to support all fitness devices that can be represented by a set of scalar and vector values. This interface provides a general solution to detect hardware, query it for available parameters, their access permissions, and then allows the user to set and retrieve these values. The items of interest when using a treadmill, for example, would be speed, incline and time elapsed; with a bicycle one might want speed and a resistance profile. This interface also provides functionality for device synchronization, and the registration of callbacks used for notification purposes. The level of abstraction in this layer shields the user from the various communication protocols employed by different fitness devices and presents a uniform interface which accommodates future devices.

In alternative embodiments iExercise provides additional interfaces that include the following functionality: Fitness device detection and enumeration, simulation of terrain segments expressed in terms of distance and gradient, recording of session parameters such as heart rate, distance traveled, calories expended, workout duration etc., and miscellaneous clocks and timers. In alternative embodiments several common supporting interfaces are available. These allow access to advanced functionality and information about the user.

In the preferred embodiments the interval callback allows the application to support user-specified exercise sessions. The user can set features such as minimum warm-up time, number of intervals, interval length, time or recovery requirements (e.g., heart rate below some rate) between intervals, and minimum warm-down time. Applications registering for interval callbacks will be provided with this data, as well as callbacks when intervals should begin and end. In the preferred embodiment the exercise data, such as miles traveled, calories burned, average intensity, etc. are all available through the data interface. In the preferred embodiment override callbacks are provided for several cases. These cases include the user's changing a device setting, such as incline or speed, or some other condition as indicated in the result code.

In the preferred embodiment the application may not be asked to access user data. However, it is available to the application if desired. The user data structure is as defined in the interface header files.

In the preferred embodiment a data-acquisition module (DAM) forms the interface between the exercise device and the IExercise middleware. Sensors on the exercise device monitor variables such as speed, heart-rate, incline, etc. and these are fed into the DAM which in turn provide these to the IExercise API. The DAM is compatible with fitness equipment from the major manufacturers and provides a seamless interface across diverse hardware platforms.

The IExercise API is preferably comprised of several closely related objects that can be used in different configurations to achieve the following: allow a USER to interact with a MACHINE within a given CONTEXT. The USER is a representation of a person, and to represent that person, information of the following kind is needed: Height, weight, age, sex, fitness level, workout goals etc. The MACHINE is a representation of a device such as a bike, a treadmill, an elliptical trainer, etc. and to represent that device, information of the following kind is needed: Can you set speed, incline, resistance? Can you retrieve information such as heart rate, power, etc. This information differs by device. The CONTEXT is a representation of a particular application that the USER is immersed in, and could be a race simulation, a shoot'em up game, a weight-loss workout. The IExercise API currently defines the following functionality. In a preferred embodiment, code implementing the IExercise API is provided below.

```
//////////////////////////////////////////////////USER
typedef enum
{ IX_EXCELLENT,
    IX_VERY_GOOD,
    IX_GOOD,
    IX_OK,
    IX_NOT_VERY_GOOD,
} IX_FITNESS_CONDITION;
typedef enum
{ IX_100,
    IX_90,
    IX_80,
    IX_70,
    IX_60,
    IX_50,
    IX_40,
    IX_30,
    IX_20,
    IX_10,
    IX_0,
} IX_LEVEL_OUTPUT;
typedef struct
{
```

-continued

```
        char                    name[IX_USER_NAME_LEN];
        unsigned                short age;
        unsigned                char sex;
        float                   weight_lbs;
        float                   height_ft;
        unsigned                short target_heart_rate; //bpm
    IX_FITNESS_CONDITION        fitness_condition;
    IX_LEVEL_OUTPUT             level_output;
    unsigned char               physician_supervision;
} IX_USER_INFO;
class IX_CUserProfile
{
    public:
        IX_CUserProfile( );
        ~IX_CUserProfile( );
        HRG_RESULT Initialize(const HRG_USER_INFO *p_info);
        HRG_RESULT GetInfo(HRG_USER_INFO *p_info);
    protected:
};
///////////////////////////////////////////////////MACHINE
typedef enum
{
    IX_DEV_BIKE             = 0,
    IX_DEV_TREADMILL        = 1,
    IX_DEV_ELLIPTICAL       = 2,
    IX_DEV_STEPPER          = 3,
    IX_DEV_MAJOR_UNKNOWN    =-999
} IX_DEV_MAJOR_CLASS;
typedef enum
{
    IX_DEV_MINOR1           = 0,
    IX_DEV_MINOR2           = 1,
    IX_DEV_MINOR_UNKNOWN    =-999
} IX_DEV_MINOR_CLASS;
typedef enum
{
    IX_COMM_NONE            = 0,
    IX_COMM_GENERIC         = 1,
    IX_COMM_HRG             = 2,
    IX_COMM_CSAFE           = 3,
    IX_COMM_UNKNOWN         = -999
} IX_COMM_PROTOCOL;
typedef enum
{
    IX_AUDIO_NONE           = 0,
    IX_AUDIO_GENERIC        = 1,
    IX_AUDIO_HRG            = 2,
    IX_AUDIO_IFIT           = 3,
    IX_AUDIO_UNKNOWN        =-999
} IX_AUDIO_PROTOCOL;
typedef struct
{
        char                    device_filename[IX_FILENAME_LEN];
        char                    device_desc[IX_DESC_LEN];
        char                    model[IX_DESC_LEN];
        char                    ROM_version[IX_DESC_LEN];
        char                    manufacturer_str[IX_DESC_LEN];
    IX_DEV_MAJOR_CLASS          major_class;
    IX_DEV_MINOR_CLASS          minor_class;
    IX_COMM_PROTOCOL            comm_protocol_type;
    IX_AUDIO_PROTOCOL           audio_protocol_type;
        unsigned short          num_scalars;
        unsigned short          num_vectors;
} IX_DEV_INFO;
typedef struct
{
        unsigned char connected     : 1;
        unsigned char ready         : 1;
        unsigned char error_set     : 1;
} IX_DEV_STATUS;
typedef enum
{
    IX_NO_UNITS             = 0,
    IX_MILES_PER_HOUR       = 1,
    IX_KILOMETERS_PER_HOUR  = 2,
    IX_METERS_PER_SECOND    = 3,
    IX_WATTS                = 4,
    IX_SECONDS              = 5,
    IX_MINUTES              = 6,
```

-continued

```
    IX_HOURS                = 7,
    IX_MATRIX               = 8,
    IX_PERCENT              = 9,
    IX_BPM                  = 10,
    IX_MINUTES_PER_MILE     = 11,
    IX_MILES                = 12,
    IX_KILOMETERS           = 13,
    IX_METERS               = 14,
    IX_ITEM_UNITS_UNKNOWN   = -999
} IX_ITEM_UNITS;
typedef struct
{
    unsigned char can_set           : 1;
    unsigned char notify_on_change  : 1;
    unsigned char needs_update      : 1;
    unsigned char got_new_val       : 1;
    unsigned char read_error        : 1;
    unsigned char write_error       : 1;
}IX_ITEM_FLAGS;
typedef enum
{
    IX_SCALAR_SPEED         = 0,
    IX_SCALAR_RESISTANCE    = 1,
    IX_SCALAR_INCLINE       = 2,
    IX_SCALAR_HEART_RATE    = 3,
    IX_SCALAR_POWER         = 4,
    IX_SCALAR_UNKNOWN       = -999
} IX_SCALAR_TYPE;
typedef double          IX_SCALAR;
typedef struct
{
    IX_SCALAR min;
    IX_SCALAR max;
    IX_SCALAR delta;
} IX_SCALAR_RANGE;
typedef struct
{
    char                desc[IX_DESC_LEN];
    IX_SCALAR_TYPE      type;
    IX_SCALAR_RANGE     range;
    IX_ITEM_FLAGS       flags;
    IX_ITEM_UNITS       units;
    IX_SCALAR           value;
} IX_SCALAR_INFO;
typedef enum
{
    IX_VECTOR_RESISTANCE_PROFILE  = 0,
    IX_VECTOR_UNKNOWN   = -999
} IX_VECTOR_TYPE;
typedef struct
{
    double vector[IX_VECTOR_ROWS][IX_VECTOR_COLS];
} IX_VECTOR;
typedef struct
{
    char                desc[IX_DESC_LEN];
    IX_VECTOR_TYPE      type;
    IX_ITEM_FLAGS       flags;
    IX_ITEM_UNITS       units;
    IX_VECTOR           value;
} IX_VECTOR_INFO;
typedef unsigned short IX_DEV_ID;
typedef void(*IX_SCALAR_CALLBACK) (unsigned short   item_index,
                                   const IX_SCALAR  *p_scalar_value,
                                   unsigned char    read_error,
                                   unsigned char    write_error);
typedef void(*IX_VECTOR_CALLBACK) ( unsigned short  item_index,
                                    const IX_VECTOR *p_vector_value,
                                    unsigned char   read_error,
                                    unsigned char   write_error);
class IX_CDeviceEnumerator
{
    public:
        HRG_RESULT EnumSupportedDevices(unsigned short *p_num_devices);
        HRG_RESULT EnumSupportedDevicesByClass( IX_DEV_MAJOR_CLASS  device_class,
                                                unsigned short      *p_num_devices);
        HRG_RESULT GetSupportedDeviceInfo( unsigned short   index,
IX_DEV_INFO                                                 *p_device_info);
        HRG_RESULT EnumConnectedDevices(unsigned short *p_num_devices);
```

```
    HRG_RESULT EnumConnectedDevicesByClass( IX_DEV_MAJOR_CLASS    device_class,
                                             unsigned short                 *p_num_devices);
    HRG_RESULT GetConnectedDeviceInfo( unsigned short     index,
                             IX_DEV_ID               *p_device_id,
                             IX_DEV_INFO             *p_device_info);
    Protected, private functions and data deleted in the interest of space
};
class IX_CDeviceComm
{
  public:
    HRG_RESULT Initialize( IX_DEV_ID      device_id,
                         const IX_DEV_INFO *p_info,
                         const char         *p_sw_emulation_dir);
    HRG_RESULT GetDeviceInfo(IX_DEV_INFO *p_info);
    HRG_RESULT GetDeviceStatus(IX_DEV_STATUS *p_status);
    HRG_RESULT GetScalarValue( unsigned short index,
                             IX_SCALAR         *p_value );
    HRG_RESULT GetScalarInfo(unsigned short index,
                             IX_SCALAR_INFO      *p_info);
    HRG_RESULT SetScalarValue(unsigned short             index,
                             const IX_SCALAR        *p_value);
    HRG_RESULT RegisterScalarCallback(IX_SCALAR_CALLBACK    p_callback);
    HRG_RESULT TurnOnScalarNotification( unsigned short index);
HRG_RESULT TurnOffScalarNotification( unsigned short index);
    HRG_RESULT GetVectorValue( unsigned short        index,
                             IX_VECTOR         *p_value );
    HRG_RESULT GetVectorInfo( unsigned short             index,
                             IX_VECTOR_INFO          *p_info );
    HRG_RESULT SetVectorValue(unsigned short             index,
                             const IX_VECTOR         *p_value);
    HRG_RESULT RegisterVectorCallback(IX_VECTOR_CALLBACK p_callback);
    HRG_RESULT TurnOnVectorNotification( unsigned short index);
    HRG_RESULT TurnOffVectorNotification( unsigned short index);
    HRG_RESULT UpdateOutboundData( );
    HRG_RESULT UpdateInboundData( );
    Protected, private functions and data deleted in the interest of space
};
class IX_CTreadmillComm : IXCDeviceComm
{
  public:
    HRG_RESULT Initialize (IX_DEV_ID       device_id,
                         const IX_INFO     *p_info);
    HRG_RESULT StartTimer( );
    HRG_RESULT StopTimer( );
    HRG_RESULT GetElapsedSeconds(double *p_seconds);
    HRG_RESULT GetTreadmillInfo(IX_DEV_INFO *p_info);
    HRG_RESULT GeTreadmillStatus(IX_DEV_STATUS *p_status);
    HRG_RESULT GetSpeed(doulbe *p_speed);
    HRG_RESULT GetSpeedRange(IX_SCALAR_RANGE *p_range);
    HRG_RESULT GetSpeedUnits(IX_ITEM_UNITS *p_units);
    HRG_RESULT SetSpeed(double speed);
    HRG_RESULT GetIncline(double *p_incline);
    HRG_RESULT GetInclineRange((IX_SCALAR_RANGE *p_range);
    HRG_RESULT GetInclineUnits(IX_ITEM_UNITS *p_units);
    HRG_RESULT SetIncline(double incline);
    HRG_RESULT GetHeartRate(double *p_heart_rate);
    HRG_RESULT GetHeartRateRange(IX_SCALAR_RANGE *p_range);
    HRG_RESULT GetHeartRateUnits(IX_ITEM_UNITS *p_units);
    HRG_RESULT GetPower(double *p_power);
    HRG_RESULT GetPowerRange(IX_SCALAR_RANGE *p_range);
    HRG_RESULT GetPowerUnits(IX_ITEM_UNITS *p_units);
    HRG_RESULT GetPace(double *p_pace);
    HRG_RESULT GetPaceRange(IX_SCALAR_RANGE *p_range);
    HRG_RESULT GetPaceUnits(IX_ITEM_UNITS *p_units);
    HRG_RESULT SetPace(double pace);
    HRG_RESULT GetVDistance(double *p_vdistance);
    HRG_RESULT GetVDistanceUnits(IX_ITEM_UNITS *p_units);
    HRG_RESULT GetHDistance(double *p_hdistance);
    HRG_RESULT GetHDistanceUnits(IX_ITEM_UNITS *p_units);
    HRG_RESULT SetNotification(IX_SCALAR_CALLBACK p_callback);
};
class IX_CBikeComm : IXCDeviceComm
{
  public:
    HRG_RESULT Initialize(IX_DEV_ID device_id,
                         const IX_INFO *p_info);
    HRG_RESULT StartTimer( );
    HRG_RESULT StopTimer( );
    HRG_RESULT GetElapsedSeconds(double *p_seconds);
```

```
        HRG_RESULT GetBikeInfo(IX_DEV_INFO *p_info);
        HRG_RESULT GetBikeStatus(IX_DEV_STATUS *p_val);
        HRG_RESULT GetSpeed(double *p_speed);
        HRG_RESULT GetSpeedRange(IX_SCALAR_RANGE *p_range);
        HRG_RESULT GetSpeedUnits(IX_ITEM_UNITS *p_units);
        HRG_RESULT GetResistance(double *p_resistance);
        HRG_RESULT GetResistanceRange(IX_SCALAR_RANGE *p_range);
        HRG_RESULT GetResistanceUnits(IX_ITEM_UNITS *p_units);
        HRG_RESULT SetResistance(double resistance);
        HRG_RESULT GetHeartRate(double *p_heart_rate);
        HRG_RESULT GetHeartRateRange(IX_SCALAR_RANGE *p_range);
        HRG_RESULT GetHeartRateUnits(IX_ITEM_UNITS *p_units);
        HRG_RESULT GetPower(double *p_power);
        HRG_RESULT GetPowerRange(IX_SCALAR_RANGE *p_range);
        HRG_RESULT GetPowerUnits(IX_ITEM_UNITS *p_units);
        HRG_RESULT GetPace(double *p_pace);
        HRG_RESULT GetPaceRange(IX_SCALAR_RANGE *p_range);
        HRG_RESULT GetPaceUnits(IX_ITEM_UNITS *p_units);
        HRG_RESULT GetVDistance(double *p_vdistance);
        HRG_RESULT GetVDistanceUnits(IX_ITEM_UNITS *p_units);
        HRG_RESULT GetHDistance(double *p_hdistance);
        HRG_RESULT GetHDistanceUnits(IX_ITEM_UNITS *p_units);
        HRG_RESULT SetNotification(IX_SCALAR_CALLBACK p_callback);
HRG_RESULT GetResistanceProfile(IX_VECTOR_VALUE *p_resistance_profile);
    };
///////////////////////////////////////////////CONTEXT
class HRG_CGradCourse
{
   public:
        HRG_RESULT Initialize( const char               *p_description,
                               unsigned long            num_segments,
                               const HRG_DIST_GRAD_SEGMENT   *p_segments);
        HRG_RESULT InitializeFromFile(const char *filename);
        HRG_RESULT SaveToFile(const char *p_filename);
        HRG_RESULT GetCourseDistance(float *p_distance);
        HRG_RESULT GetNumSegments(unsigned long *p_num_segments);
        HRG_RESULT GetSegmentInfo( unsigned long           segment_index,
                               HRG_DIST_GRAD_SEGMENT *p_segment_info);
        HRG_RESULT GetSegmentGradient( unsigned long   segment_index,
                               float                   *p_gradient);
        HRG_RESULT GetSegmentDistance( unsigned long segment_index,
                               float                   *p_distance);
        HRG_RESULT GetMaxGradient(float *p_gradient);
        HRG_RESULT GetMinGradient(float *p_gradient);
        HRG_RESULT GetAvgGradient(float *p_gradient);
        HRG_RESULT GetNumUphillSegments(unsigned long       *p_num_segments);
        HRG_RESULT GetNumDownhillSegments(unsigned long   *p_num_segments);
        HRG_RESULT GetNumFlatSegments(unsigned long         *p_num_segments);
        HRG_RESULT GetDistanceBeforeSegment(unsigned long segment_index,
                               float *p_distance);
        HRG_RESULT GetSegmentIndex(float distance,
                               unsigned long *segment_index);
};
class HRG_CCourseHelper
{
    public:
        HRG_RESULT GetRunRise( const HRG_DIST_GRAD_SEGMENT   *p_dg,
                               HRG_RUN_RISE_SEGMENT          *p_rr);
        HRG_RESULT GetDistGrad( const HRG_RUN_RISE_SEGMENT   *p_rr,
                               HRG_DIST_GRAD_SEGMENT         *p_dg);
};
class HRG_CClock
{
    public:
        HRG_RESULT GetTimeSeconds(double *p_time);
};
class HRG_CTimer
{
    public:
    HRG_CTimer( );
    ~HRG_CTimer( );
    HRG_RESULT Start( );
    HRG_RESULT GetElapsedSeconds(double *p_elapsed_secs);
    HRG_RESULT GetElapsedMilliseconds(unsigned long *p_elapsed_millisecs);
};
class HRG_CTimeValueRecorder
{
    public:
        HRG_RESULT InitializeRecording(unsigned long max_items);
```

-continued

```
        HRG_RESULT Record(float current_value);
        HRG_RESULT GetNumItems(unsigned long *p_num_items);
        HRG_RESULT GetItem( unsigned long        item_index,
                            HRG_TIME_VALUE_FLOAT *p_item);
};
class HRG_COdometer
{
  public:
        HRG_RESULT Start(float velocity);
        HRG_RESULT UpdateVelocity(float velocity);
        HRG_RESULT GetInfo(HRG_ODOMETER_INFO *p_info);
};
//////////////////////////////////////////SOUND
#define S_MAX_DRIVERS 10
#define S_NAME_LEN      32
#define S_DESC_LEN     128
#define S_DIR_LEN      128
#define S_PATH_LEN     256
#define S_COLOR_LEN      7
#define S_COMMENT_LEN 1024
typedef enum
{ S_ERROR_OK                          = 1,
  S_ERROR_NOT_INITIALIZED             = -10,
  S_ERROR_COULD_NOT_INITIALIZE        = -11,
  S_ERROR_INVALID_PARAMS              = -12,
  SB_ERROR_NOT_INITIALIZED            = -20,
  SB_ERROR_COULD_NOT_INITIALIZE       = -21,
  SB_ERROR_CREATE                     = -23,
  SB_ERROR_RELEASE                    = -24,
  SB_ERROR_GET_FREQUENCY              = -25,
  SB_ERROR_GET_PAN                    = -26,
  SB_ERROR_GET_VOLUME                 = -27,
  SB_ERROR_PLAY                       = -28,
  SB_ERROR_SET_FREQUENCY              = -29,
  SB_ERROR_SET_PAN                    = -30,
  SB_ERROR_SET_VOLUME                 = -31,
  SB_ERROR_STOP                       = -32,
  SB_ERROR_LOCK                       = -33,
  SB_ERROR_UNLOCK                     = -34,
  SB_ERROR_INVALID_PARAMS             = -35,
  SB_ERROR_REWIND                     = -36,
  SB_ERROR_GET_PLAY_POSITION          = -37,
  SB_ERROR_SET_PLAY_POSITION          = -38,
  WAV_ERROR_NOT_INITIALIZED           = -50,
  WAV_ERROR_INVALID_PARAMS            = -51,
  WAV_ERROR_COULD_NOT_INITIALIZE      = -52,
  WAV_ERROR_COULD_NOT_FIND            = -53,
  WAV_ERROR_COULD_NOT_LOAD            = 54,
       WAV_ERROR_COULD_NOT_LOCK       = -55,
} S_ERROR;
typedef struct
   {
     GUID Id;
     char Desc[S_DESC_LEN];
   } S_DRIVER_INFO;
typedef struct
   { S_DRIVER_INFO Item[S_MAX_DRIVERS];
     unsigned int NumDrivers;
   } S_DRIVERS;
typedef enum
   { SB_MODE_PLAY_LOOP,
     SB_MODE_PLAY_NO_LOOP
   } SB_PLAY_MODE;
class CDSSound
{
  public:
    S_ERROR GetNumDrivers(unsigned int *NumDrivers);
    S_ERROR GetDriverInfo(unsigned int DriverIndex, S_DRIVER_INFO *Info);
    S_ERROR Initialize(HWND hAppWindow, S_DRIVER_INFO *Info);
    S_ERROR GetDSPointer(LPDIRECTSOUND *pDS);
    S_ERROR Destroy( );
};
class CDSSoundBuffer
{
  public:
    S_ERROR Create(LPDIRECTSOUND pDS, WAVEFORMATEX *pFormat, unsigned
    long BufferSize);
    S_ERROR Destroy( );
    S_ERROR Fill(const BYTE *pData, unsigned long DataSize);
```

-continued

```
        S_ERROR GetFrequency(DWORD *Frequency);
        S_ERROR GetPan(long *PanValue);
        S_ERROR GetPlayPosition(DWORD *PlayPosition);
        S_ERROR GetPlayMode(SB_PLAY_MODE *PlayMode);
        S_ERROR GetVolume(long *Volume);//value of 0 to -10 000
        BOOL IsBufferPlaying( );
        S_ERROR Play( );
        S_ERROR Rewind( );
        S_ERROR SetFrequency(DWORD Frequency);
        S_ERROR SetPan(long PanValue);
        S_ERROR SetPlayPosition(DWORD PlayPosition);
        S_ERROR SetPlayMode(SB_PLAY_MODE PlayMode); //Primary buffers must be
        set to SB_MODE_PLAY_LOOP
        S_ERROR SetVolume(long Volume); //value of 0 to -10 000
        S_ERROR Stop(void);
    };
class CWaveSound
{
    public:
        S_ERROR Destroy( );
        S_ERROR GetData(BYTE *pData unsigned long MaxByteSize);
        S_ERROR GetFormat(WAVEFORMATEX *WaveFormat);
        S_ERROR GetName(char *pName, unsigned long MaxLength);
        S_ERROR GetSize(unsigned long *WavByteSize);
        S_ERROR InitializeFromResource(const char *ResourceName);
        S_ERROR InitializeFromFile(const char *FileName);
};
class CDSWavPlayer
{
    public:
        int PlayWavFile(LPDIRECTSOUND pDS, const char* FullWavPath);
        int Destroy( );
};
class HRG_CSineWaveGenerator
{
    public:
        HRG_RESULT Initialize(unsigned long sine_frequency,       //Hz
                              unsigned long sampling_frequency,   //Hz
                              unsigned long duration,             //milli seconds
                              unsigned long amplitude_multiplier);
        HRG_RESULT GetNumSamples(unsigned long *p_num_samples);
        HRG_RESULT GetSamples(double *p_sample_array,
unsigned long array size);
        HRG_RESULT GetSample(unsigned long sample_index,
double *p_sample);
};
class HRG_CIFitChirper
{
    public:
        HRG_RESULT Initialize( );
        HRG_RESULT CreateChirp( double speed,
                                double incline);
        HRG_RESULT PlayChirp(LPDIRECTSOUND pDS);
        HRG_RESULT SaveChirp(const char *p_filename);
        HRG_RESULT Destroy( );
};
```

The preferred embodiment enriches the fitness/entertainment experience by taking the human factor into account. The users of exercise equipment come in all shapes and sizes, have different skill levels and levels of fitness, and have differing needs. The preferred embodiment provides application developers with much information about the user as is needed in order to create content that is engaging and in which gameplay is fair when matching opponents with different skill levels.

The preferred embodiment can combine USB-compliant hardware and a high-level software API that provides a cross-platform solution for creating games and other applications for fitness equipment such as bicycles and treadmills. This solution which can be compatible with PCs, game consoles, and a wide variety of fitness devices, offers application developers the opportunity to adopt a non-proprietary, cross-platform system.

The preferred embodiment changes the way people exercise: Fun exercise that replaces boredom; and the ability to track and manage historical workout activity. For fitness equipment vendors, the preferred embodiment provides: Product differentiation among other equipment OEMs and against existing products drives replacement of existing equipment by current customers. For workout and game publishers, the preferred embodiment enables a new interactive game platform: New life for existing games appropriate for exercise modalities, A new game genre and market opportunity—interactive fitness games.

The preferred embodiment makes the cost of doing an exercise modality trivial relative to content development costs, and the cost of integrating devices into fitness hardware also trivial.

In alternative embodiments many different modalities are possible for many different games all have common display of current intensity, intensity, heart rate, optional display of upcoming intensity, time elapsed, time remaining, etc. In some embodiments, modalities for race simulations are provided.

In an alternative embodiment there is a first-person shooter modality where you have to pedal above a minimum threshold to get more ammo, the faster you pedal, the faster you can move, and at max pedaling, can get special weapons. In an alternative embodiment there is a "Tetris"-style modality which can slow falling block by pedaling faster, "intervals" possible as blocks fall faster, and "reserve" energy allows you to destroy bottom layers. In an alternative embodiment there is a "Myst"-style modality where you have to pedal to travel around the place being explored and certain devices must be "charged."

In the preferred embodiment exercise profile initialization supports the combination of several methods of setting up initial profiles for a given user: standard defaults, either fully generic or based on upon inputs such as age, sex, and current exercise habits, medical limitations, coaching or therapeutic guidance, guidance for fitness, weight loss, etc., and other guidance appropriate to exercise plans.

Preferably, the runtime core executes most of the real-time processing, including: device equivalence; monitoring the user as indicated by the fitness plan; communication with the game, including: intensity intervals, warm-up & cool-down, current user intensity & power, and information about the user & fitness solution for display or other purposes, e.g., name, device type, etc.; and, communication with the device driver: any setup for this user and this device, device capabilities, including information to compute instantaneous watts being generated by the user, and information about the device that may be desired by the fitness records, the game, or other needs.

The preferred Universal Device Driver is a relatively large body of software compared to many other device drivers. It is charged with understanding how to communicate with the various exercise devices. Preferably, it does this through several paths: it knows how to communicate with devices supporting existing published and unpublished standards, such as CSafe and iFit, it supports a generic set of interfaces, known collectively as the iExercise Device Compliance specification, which provide standard methods for reading device state (e.g., instantaneous power output of the user), device capabilities (e.g., power curves and meaning of resistance settings), and device-specific information (e.g., a string specifying the name of the device); and standard methods for writing to the device (e.g., for setting resistance settings or other standard user setup.)

In the preferred embodiment an iExercise compliant game is simply any application, be it a true game, an exercise or race simulation, or other application that uses the iExercise API to provide a meaningful experience to a user (or users, in the case of multiplayer applications) of a fitness solution.

In the preferred embodiment an iExercise compliant device is any device supporting: the iExercise compliance specification; or a standard interface that iExercise knows how to talk with, such as CSafe (Precor et al) or iFit (Icon et al); or a direct hardware connection (such as in the demonstration system) to a USB interface. All code and interfaces mentioned in this paragraph are herein incorporated by reference.

In the preferred embodiment a "Happy User" is any person using a "Fitness Solution" described herein to for an exercise session. The described "Fitness Solution" as a whole provides for interesting exercise sessions which meet a variety of fitness or rehabilitation goals and provide meaningful experiences to the user, said experiences providing many benefits, including some or all of the following for each user: excitement and engaging exercise rather than boredom, positive feedback about progress, reduce or eliminate completely the "willpower" to start and maintain an exercise program, and mental training (e.g., racing a specific Tour de France hill-climb against Lance Armstrong's best time ever) unavailable through traditional means.

The preferred runtime core provides two preferred elements for removing dependencies: (1) device equivalence conversion between the different device models supported by the Universal Device Driver and proper initialization of all device types based on direction of the training profile and activity software; and (2) API equivalence between applications, preferably by translating between multiple programming models attractive to various activity developers. Two examples are a pure intensity model, and a slope/weight/speed model. By so providing a standard interface to a standard training profile, exercise activities do not have to display their own UI for each session, which would cause their own problems (e.g., user has to learn new interface for each activity, knowledge of previous exercise sessions would be lost or mis-interpreted by each new activity, some exercise profile types may not be supported by all activities, activity developers would have to be conversant with all the medical/athletic issues involved with exercise planning, and monitoring the user as indicated by the fitness plan).

In the preferred embodiment, an iExercise compliant activity is a game, an exercise or race simulation, or other application that uses the iExercise API to provide a meaningful, realistic, engaging and immersive experience to a user (or users, in the case of multiplayer applications) of a fitness solution. Because these applications use the preferred embodiment, they do not have to: build their own model of the user and the user's needs, including all of the relevant UI and coaching/medical over-rides, support individually coded interfaces for every single device they want to support, and incorporate medical, athletic, and other training knowledge into the activity.

In the preferred embodiment the iExercise Universal device driver handles communication between the Runtime core and the device itself. Thus, preferably, after device-specific initialization, which involves a handshake of the device-specific data, only a relatively small amount of data needs to be exchanged. This "run-time" data includes the setting of intensity level by the driver, and the reading from the device data such as speed, additional axes of freedom, device supported user status such as heart rate, perceived exertion, oxygen uptake, etc.

FIG. 1 is a Conventional bicycle 20 installed in rear-wheel trainer 21. Under the front wheel 22 is a device 23 which uses a joystick to measure how much the front wheel is or is not turned. The small red box 24 in front of that device is a USB interface 25 which reads the rear-wheel speed and transmits it to the host computer.

Figure 2:
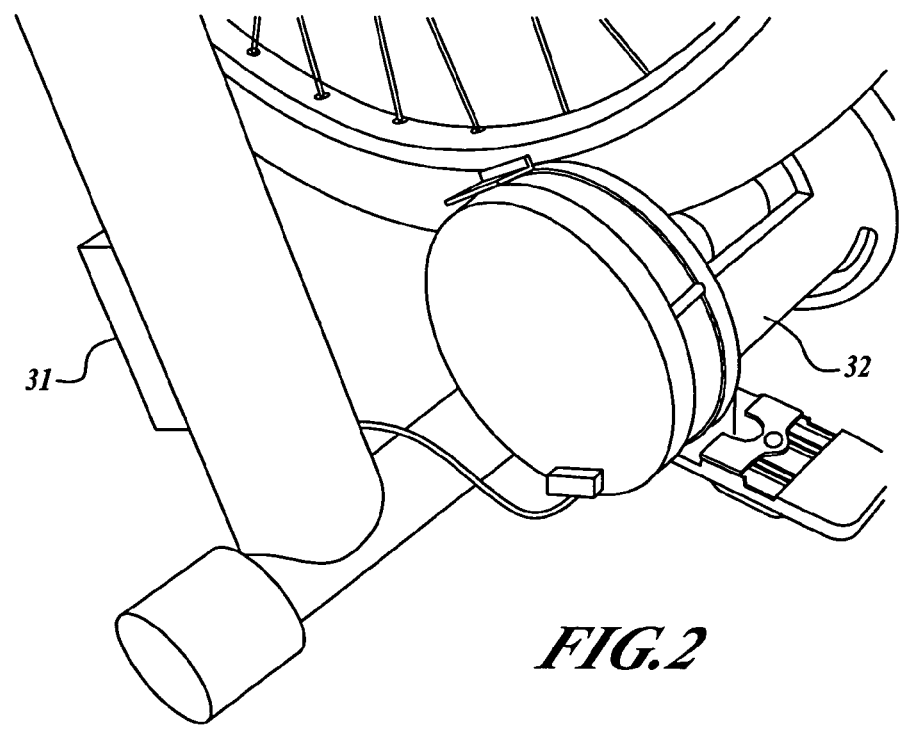
FIG. 2 is a the blue cover of the fly wheel on a rear-wheel trainer.

FIG. 2 is the blue cover of the fly wheel on a rear-wheel trainer 32. This is a commercially available rear-wheel trainer from Minoura which has been modified as a demonstration of the system. The wiring and small object at the bottom of the fly wheel cover is for a reflective infrared sensor, which includes an infrared LED and pickup. The electronics for driving the LED are in the black box 31 hidden behind the leg of the rear-wheel trainer with the www.minoura.jp sticker.

Figure 3:
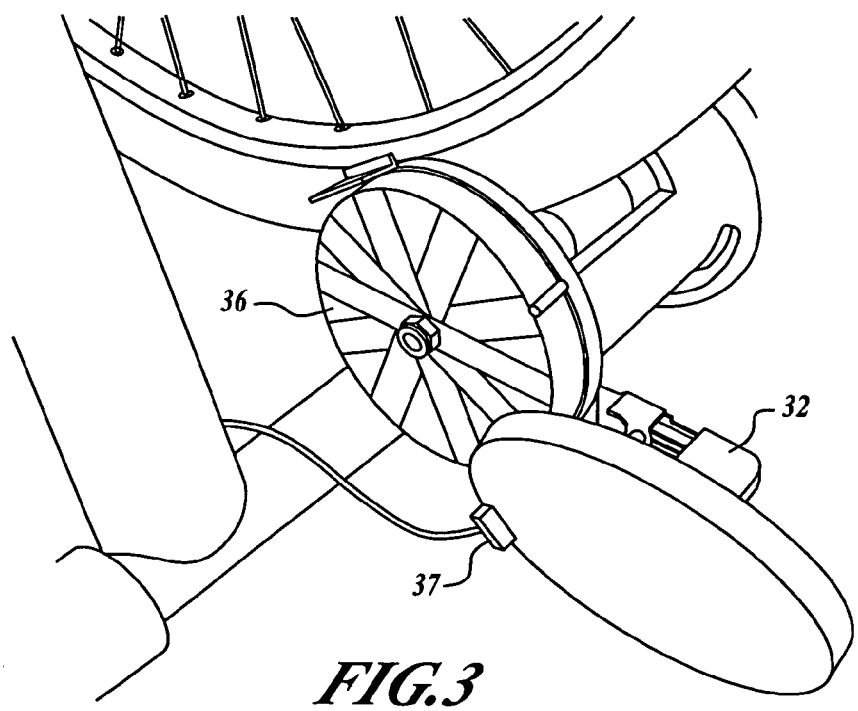
FIG. 3 is the view of the fly wheel with the cover removed.

FIG. 3 is the view of the fly wheel with the cover 32 removed. The wiring 37 connecting the infrared sensor is clearly visible, as is the black and white pattern 36 on the fly wheel which allows the sensor to detect the fly wheel's speed.

Figure 4:
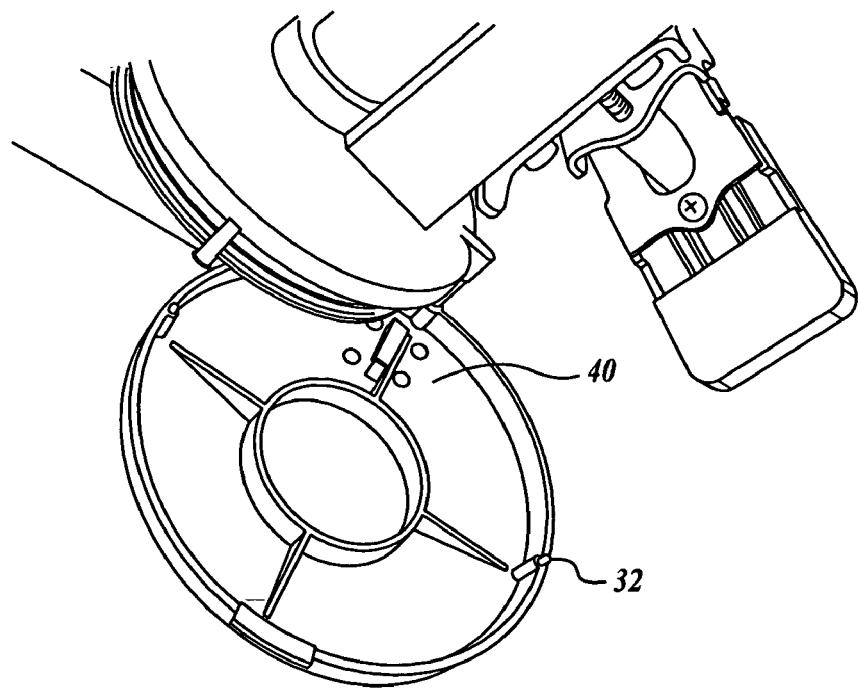
FIG. 4 is a view of the inside of the fly wheel cover showing the reflective infrared sensor.

FIG. 4 is a view of the inside of the fly wheel cover 32 showing the reflective infrared sensor 40. Preferably, this is a standard two part infrared sensor with an emitter & detector.

Figure 5:
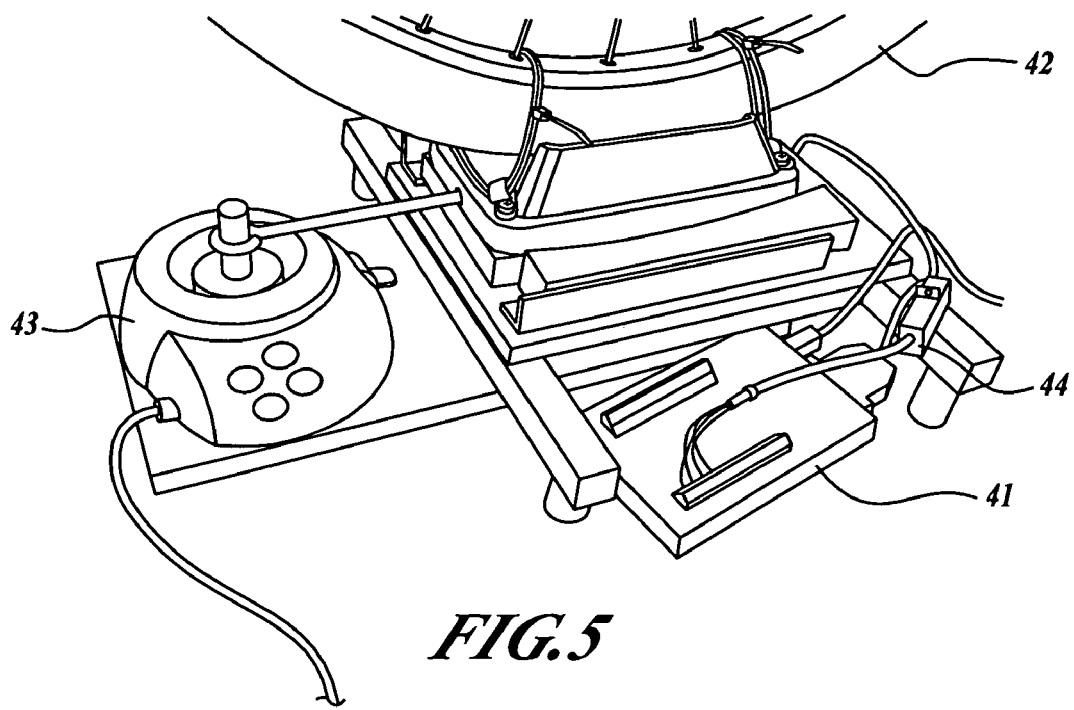
FIG. 5 is a close-up view of the assembly under the front wheel.

FIG. 5 is a close-up view of the assembly under the front wheel 42, which is a device which uses a joystick 43 to measure how much the front wheel 42 is or is not turned. The small red box 41 in front of that device is a USB interface 44 which reads the rear-wheel speed and transmits it to the host computer.

Figure 6:
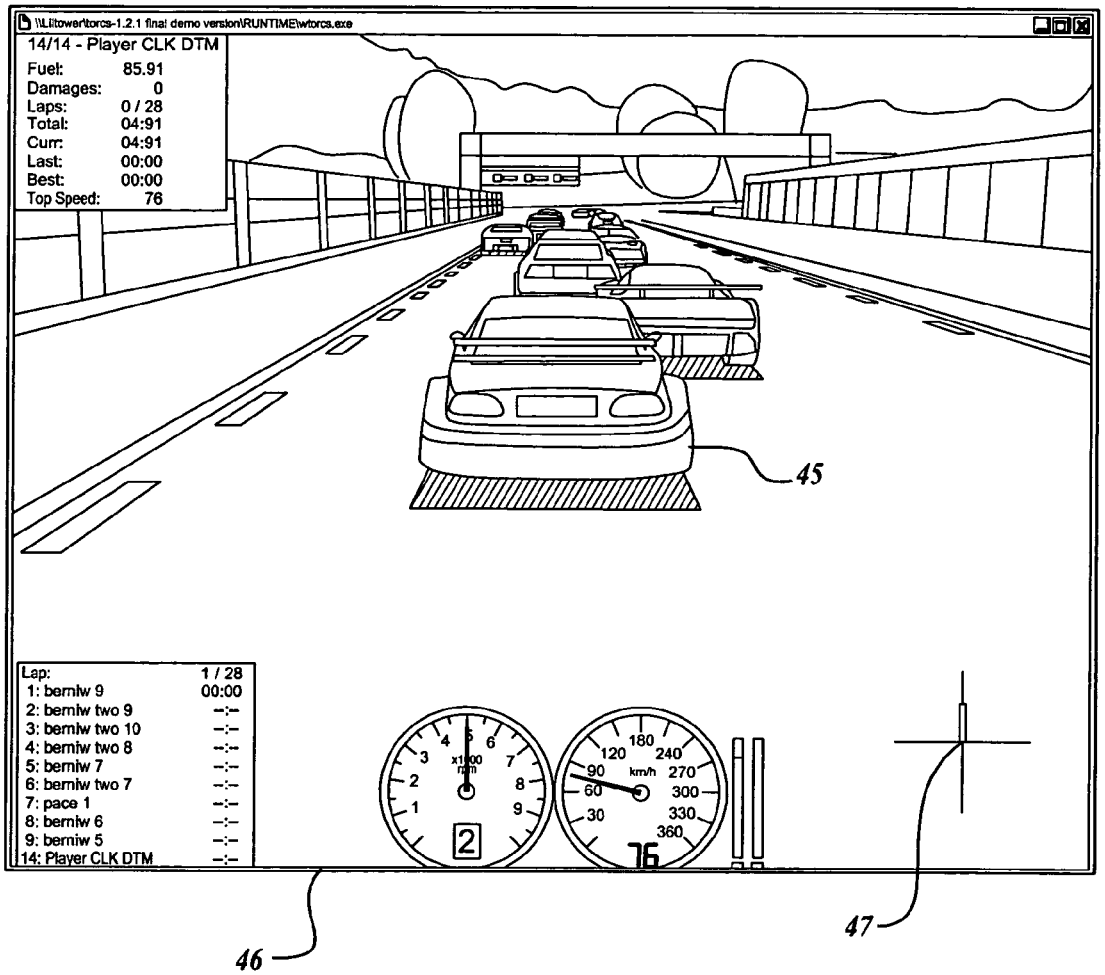
FIG. 6 is a the start of an example interactive fitness game.

FIG. 6 is the start of an example interactive fitness game. The user on a bicycle is driving the yellow car 45 seen on the center of the screen 46. A two-axis "debug graph" 47 on the bottom right of the screen shows acceleration (positive vertical axis), braking (negative vertical axis) and turning (left and right horizontal axis.) In this example, as the user pedals faster, the game model responds as if the car's accelerator pedal was depressed in direct correlation to the speed of the rear wheel of the bicycle. If the user brakes with the bicycle's brakes, the system detects this and applies the brakes of the car in proportion to the rate of slowing of the rear wheel, i.e., in proportion to how hard the user applies the brakes.

Figure 7:
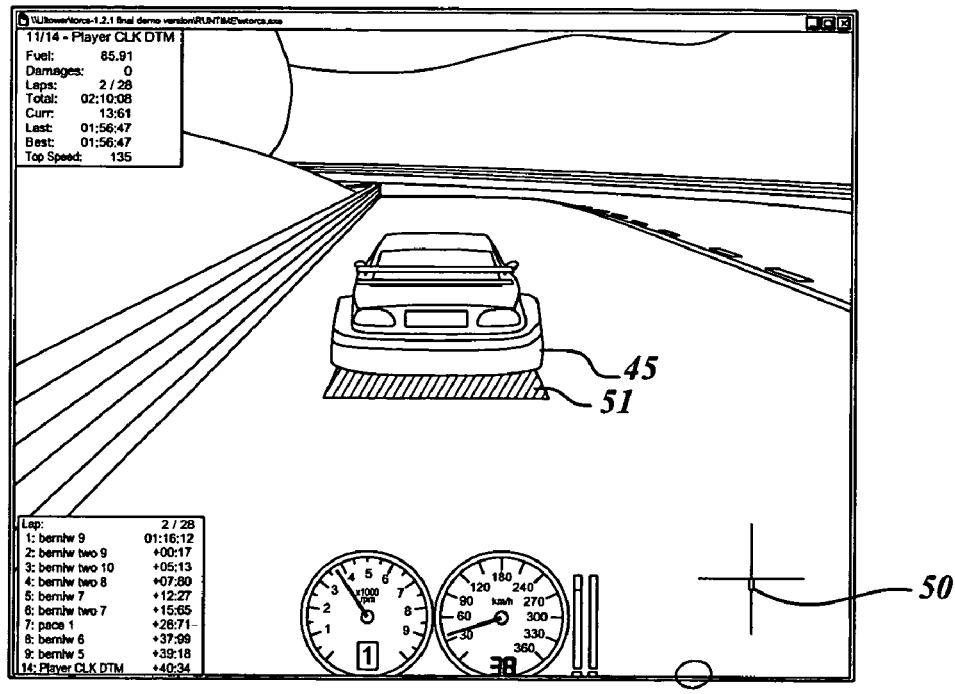
FIG. 7 is an example racing game.

FIG. 7 is an example racing game. The user on the bicycle is driving the yellow car 45 seen in the center of the screen. The user has applied the brakes on the bicycle, which the system has detected as shown by the small blue bar 50 in the negative vertical axis of the graph at the bottom right of the screen. Note the skid marks 51 just starting underneath the car.

Figure 8:
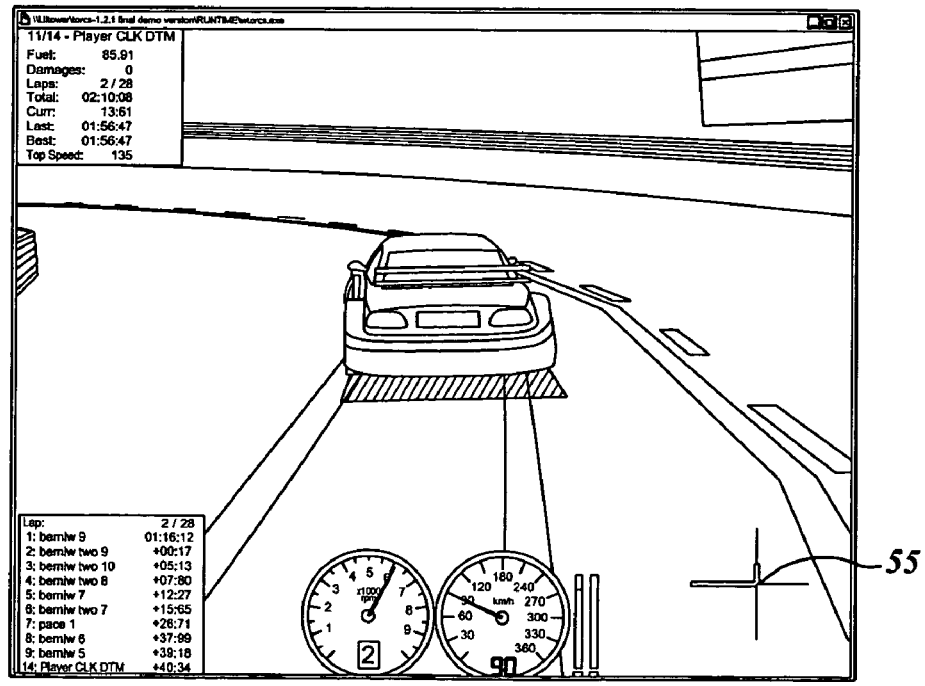
FIG. 8 shows the car accelerating through a turn.

FIG. 8 shows the car accelerating through a turn. The user on the bicycle has turned the front wheel all the way to the left, as shown by the blue bar 55 in the horizontal axis of the graph at the bottom right of the screen, and is pedaling away as shown by the blue bar 55 in the positive vertical axis.

Figure 9:
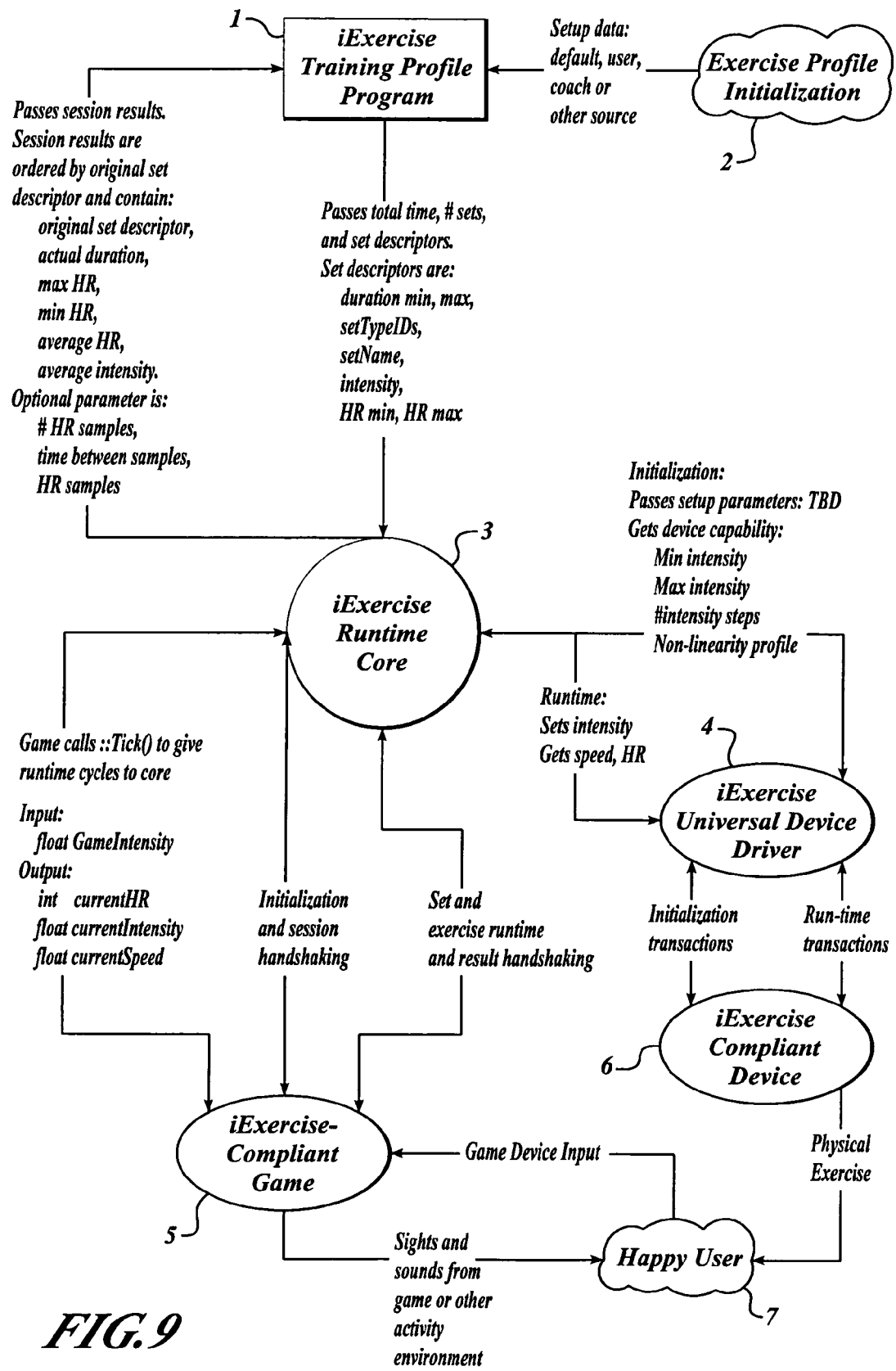
FIG. 9 describes the overall layout of the preferred software solution, allowing fitness manufacturers, game developers, and fitness professionals to understand the solution and how to work with it.

FIG. 9 describes the overall layout of the iExercise software solution, allowing fitness manufacturers, game developers, and fitness professionals to understand the iExercise solution and how to work with it. The iExercise training profile program handles the updating of user training profiles based on the initial conditions set in Block 2, Exercise Profile Initialization, and the results of each exercise session as recorded by Block 3, the iExercise runtime core. Further explanation of the succeeding blocks is provided on the Figure itself (see 1-7).

Figure 10:
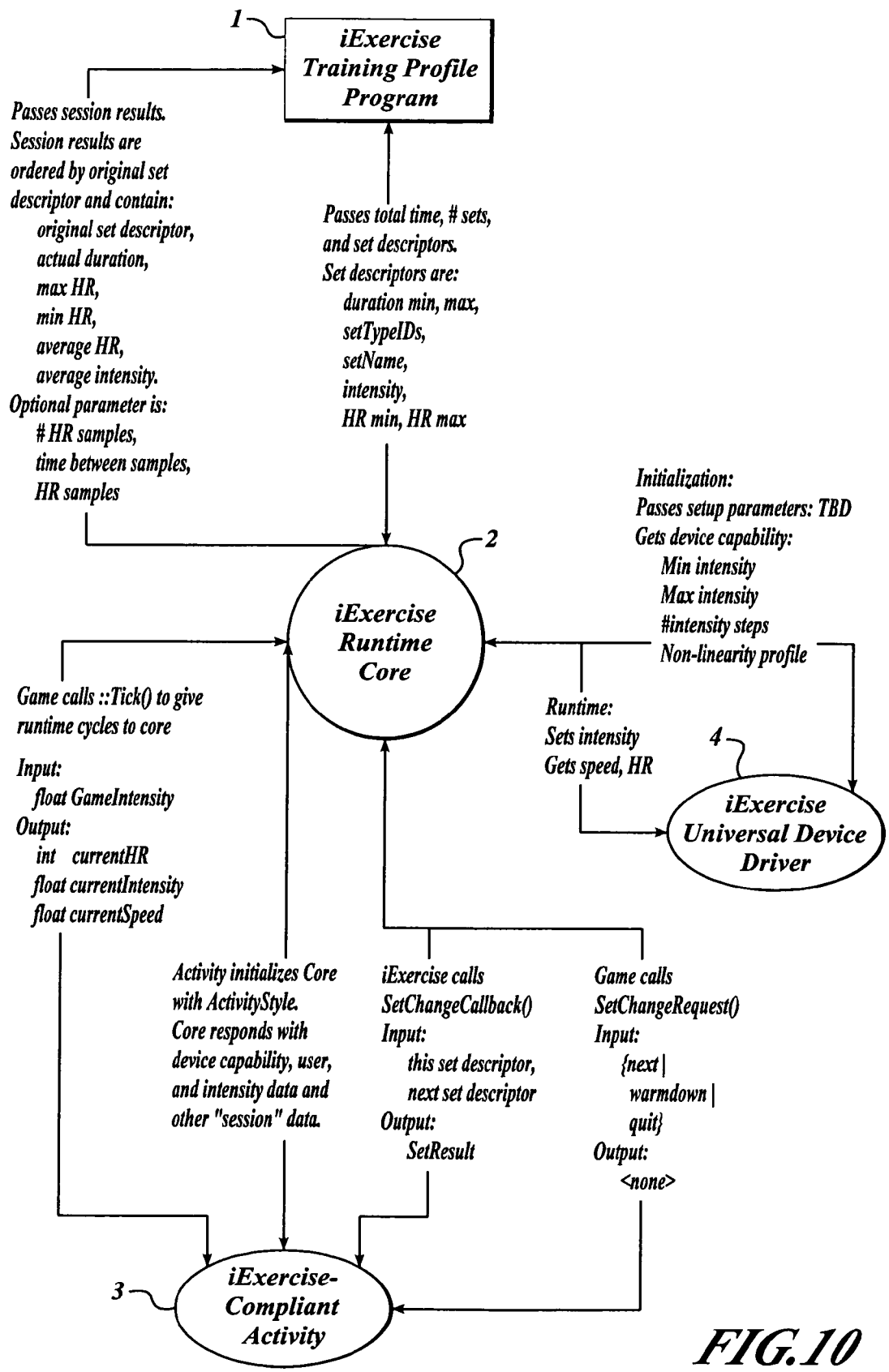
FIG. 10 shows how a preferred embodiment allows any device to work with any application, without requiring any modification or work by the end user; this makes a preferred embodiment applications and devices "Plug and Play", preferably by using a runtime core that removes all dependencies between devices and applications.

FIG. 10 shows how iExercise allows any device to work with any application, without requiring any modification or work by the end user. This makes iExercise applications and devices "Plug and Play." The iExercise training profile program handles the updating of user training profiles (initialized as described in FIG. 9) based the results of each exercise session as recorded by Block 2, the iExercise runtime core. Data to do this is passed both ways between block 1 and block 2 as shown in the diagram. Further explanation of the succeeding blocks is provided on the Figure itself (see 1-4).

Figure 11:
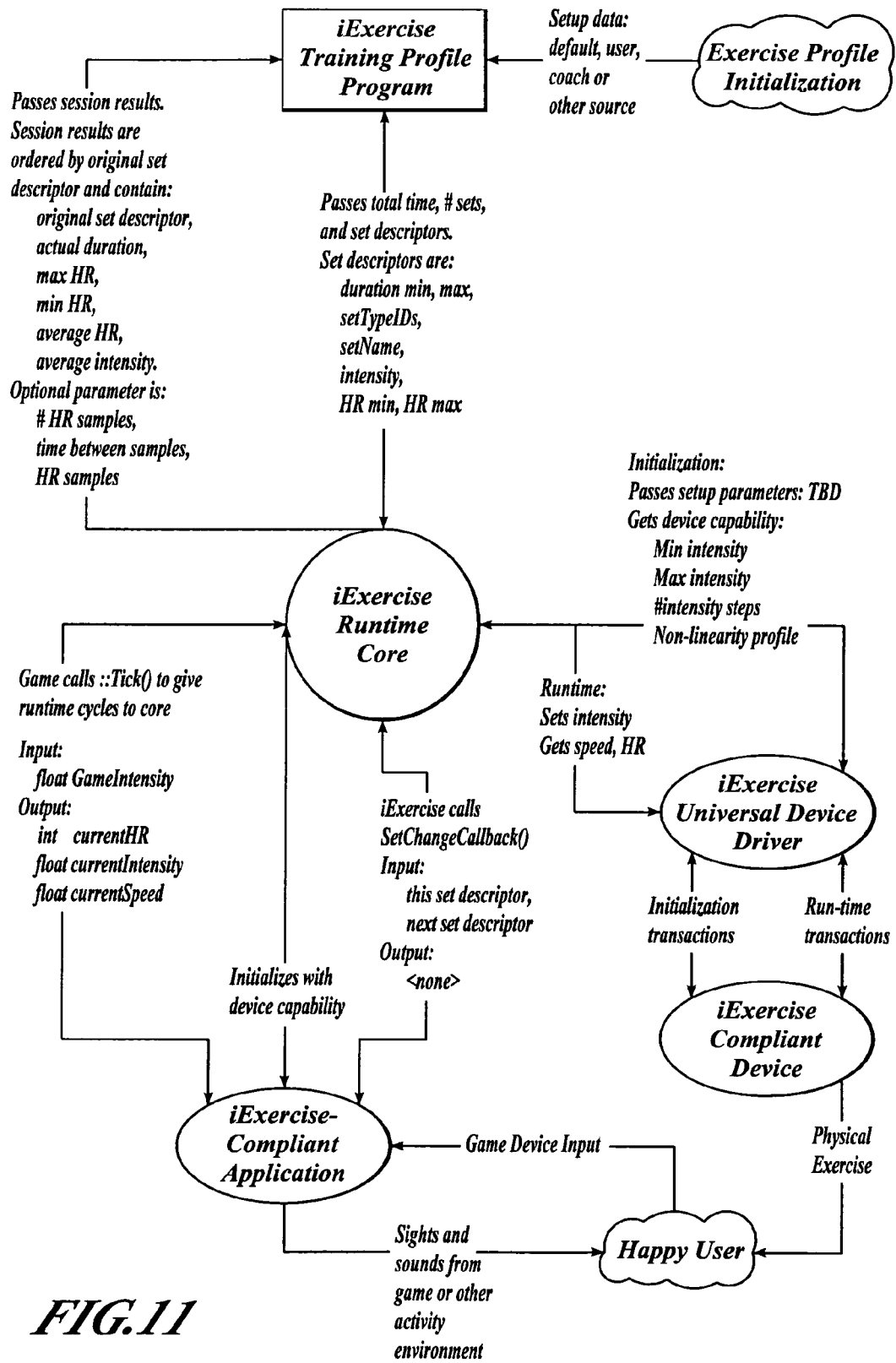
FIG. 11 is an alternative embodiment of the typical functions used and the typical path followed through the system.

FIG. 11 is an alternative embodiment of the typical functions used and the typical path followed through the iExercise system. This figure further explains how a training profile is setup as it relates each compliant device and compliant application. Explanation of the flowchart nodes or blocks are provided on the Figure itself.

Figure 12:
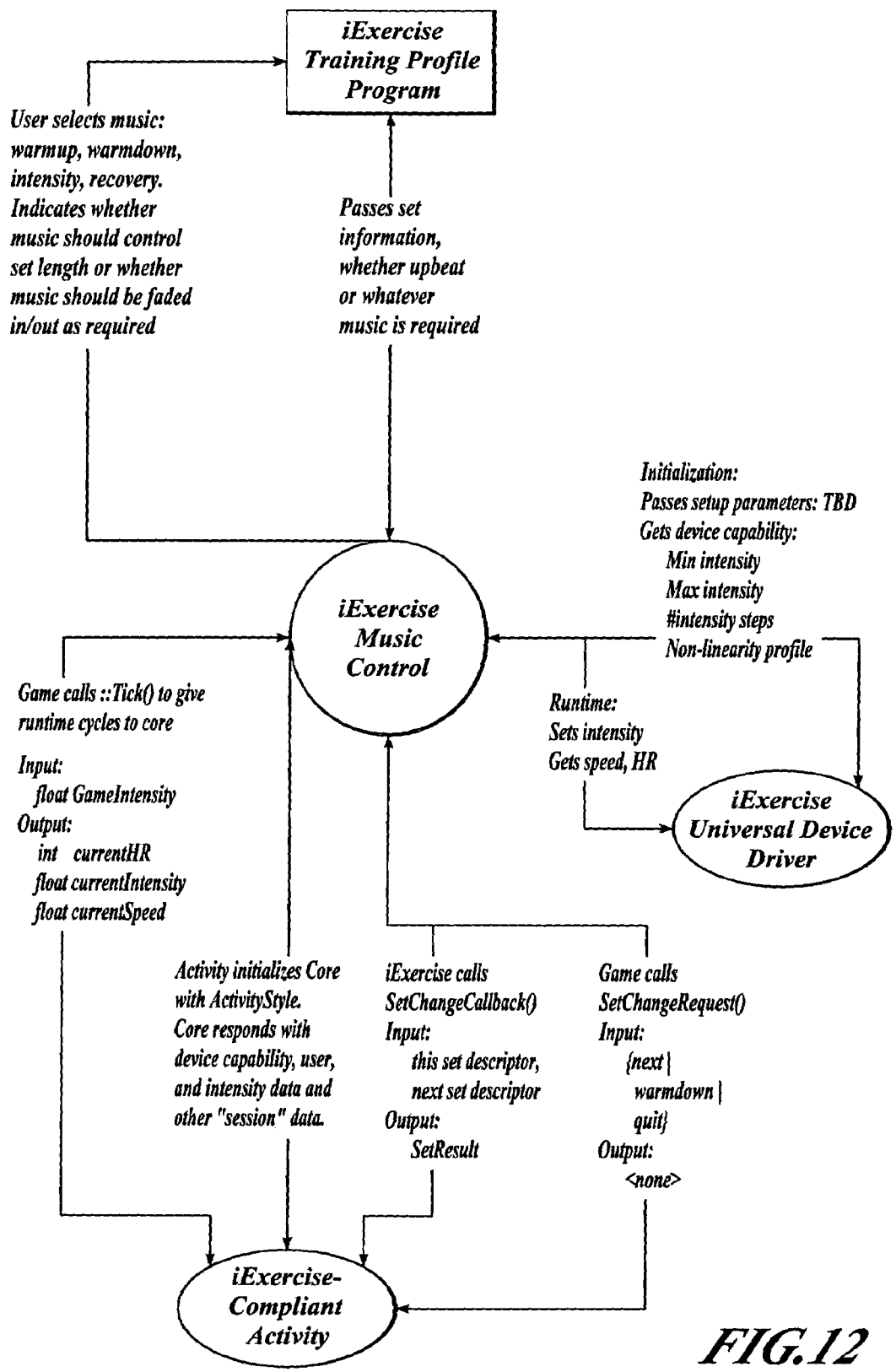
FIG. 12 shows a preferred embodiment runtime core that preferably removes all dependencies between devices and applications involving a music control.

FIG. 12 shows the preferred runtime core removes all dependencies between devices and applications involving a iExercise music control. This figure further illustrates how the preferred embodiment allows the user to select music during all parts of the workout and allows for the music to be faded in and out. Explanation of the flowchart nodes or blocks are provided on the Figure itself. The preferred iExercise music control represents an extension class of the iExercise API as described in elements 2.1-2.3 of FIG. 13 (described below). The preferred embodiment optionally includes this music control feature because music can be a valuable companion to exercise for many people, and this music control enables users to describe the "soundtracks" that should accompany their activity sessions.

Figure 13A:
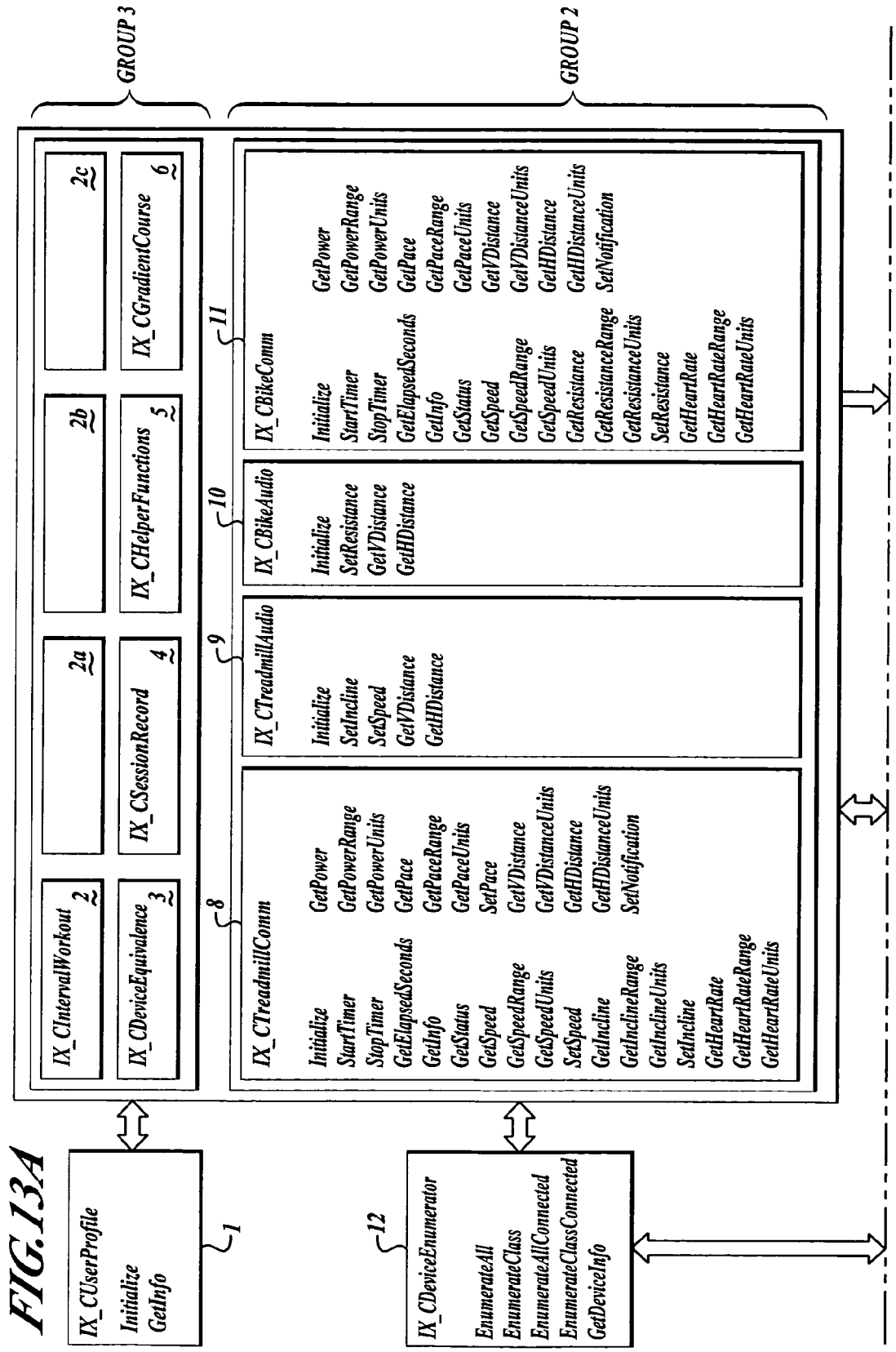
FIG. 13A illustrates a flowchart of an IX CUserProfile.

FIG. 13A shows iExercise's internal design which allows multiple device types to be integrated and made equivalent, preferably in a relatively simple equivalence layer, while simultaneously preserving device specific information in exercise records and elsewhere to meet the user's needs and for future expansion. In the preferred embodiment the iExercise training profile is defined in the class IX CUserProfile and provides static methods for initializing the profile, getting profile information including data for the current session, and setting information such as the records generated during and after completion of the current session. In the preferred embodiment class IX_CIntervalWorkout is one example of a class that is capable of reading a user profile and generating appropriate controls for an exercise session. This class generates signals to the application about when warm-up, warm-down, intensity intervals should begin and end, time or other metrics for the end of recovery times, etc. 2.1 and 2.2. are left as placeholders for future classes for new workout supports (e.g., a fat burning workout) as well as new methods for interpreting historical training records (see further, box 7 and box 6, IX_CGradientCourse).

In the preferred embodiment shown in FIG. 13A the IX_CSessionRecord captures the record of each session and is the method for examining each session record in all applications. IX_CHelperFunctions and IX_CGradientCourse can provide assistance to applications in decoding session records, as well as other functions that may be provided as extensions to the basic API.

In the preferred embodiment shown in FIG. 13A the IX_CHelperFunctions provides a number of functions that most users of the API could write themselves, but are provided for convenience and correctness. Rather than placing these functions in random places in the API (where they might not appropriate, or might be hard for the user to find) a single place was provided for them.

In the preferred embodiment shown in FIG. 13A the IX_CGradientCourse is the basic method of accessing the user's output relative to a course described as a set of gradients, each with a slope and length. The gradient course may refer either to a historical course when looking at an exercise record, or to a current exercise session. A companion API, known as Energy API is also provided but not indicated on the diagram. The Energy API is analogous to the Gradient API but provides only momentary speed or energy records in its current version.

In the preferred embodiment shown in FIG. 13A the IX_CTreadmillComm (for Communication) is responsible for communicating to treadmill class devices. As with the bike class, this class can be extended to include new devices that are comparable to treadmills. However, many devices, such as stair-steppers and elliptical trainers, may fit within the class without modification. However, entirely new classes can also be created (e.g., for isometric strength training machines.)

In the preferred embodiment shown in FIG. 13A the IX_CTreadmillAudio handles interaction with and communication to iFit-enabled treadmills. This equipment is driven by "chirps" that tell the treadmill to change speed or incline, allowing the interface to set a given exercise level for a user. Since these devices have no feedback capability to iExercise, this class also tracks the amount of work done by the user in lieu of reports from the device itself.

In the preferred embodiment shown in FIG. 13A, as with class 9, IX_CBikeAudio handles interaction with and communication to iFit-enabled bicycle trainer devices.

In the preferred embodiment shown in FIG. 13A, the IX_CBikeComm is the partner class to IX_CTreadmillComm, for stationary bicycle trainer class devices. Many other fitness devices, such as rowing machines, may end up in the bicycle trainer class. This classification is due to the resistance units common to all of them, which share the common attribute of having power-curves associated with determining watts of work being done by the exerciser. That is, an exerciser riding a bike at 10 miles an hour is doing far less than half the work of somebody riding the same bike at 20 miles an hour (given the same resistance settings.) Likewise, somebody rowing at 2 miles an hour is doing less than half the work of somebody rowing twice as fast. In all cases the actual amount of work can be deduced from the specific speed/power curve of the device, which is to be specified in the device interface read at levels 15 and 16.

Figure 13B:
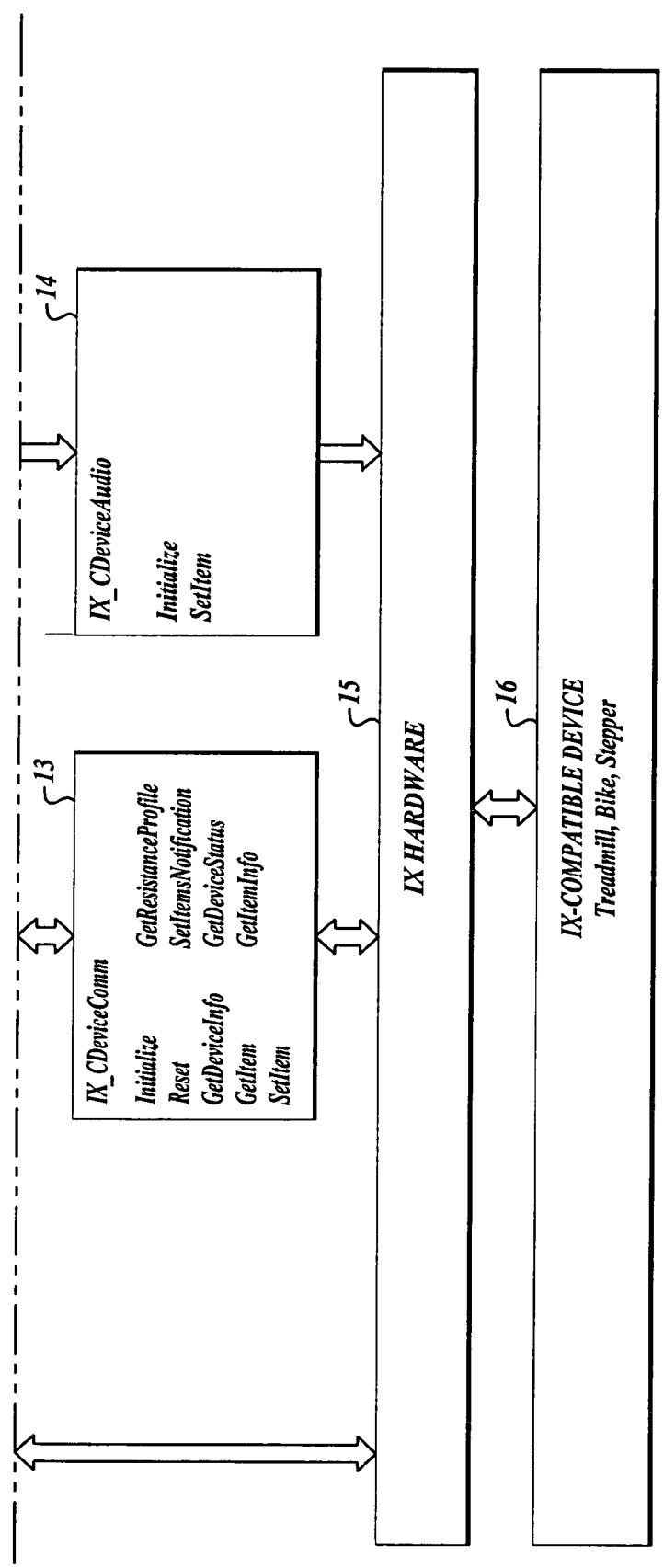
FIG. 13B illustrates an IX hardware flowchart interfaced with an IX-Compatible Device.

In the preferred embodiment shown in FIG. 13B the IX_CDeviceEnumerator is responsible for finding all IX compatible devices available on the computer or console system that will run the exercise activity. It reports information about all such devices and is capable of returning specific devices that meet the user or activity specification.

In the preferred embodiment shown in FIG. 13B the IX_CDeviceComm handles communication to all non-iFit devices. It can run on top of/over many types of device networks, such as USB, 1493 (FireWire), Bluetooth, and other device communication networks. It can also run on the device itself, if the device interface has a small microprocessor.

In the preferred embodiment shown in FIG. 13B the IX_CDeviceAudio is the layer that handles communication to all iFit devices that rely on sound as the communication medium/protocol. In the preferred embodiment shown in FIG. 13B, the IX (iExercise) Hardware comprises the hardware for interfacing to and communicating with the device. As indicated in the description of box 13, this level can be moved with respect to the communication layer and the actual device. In the preferred embodiment shown in FIG. 13B the IX (iExercise)-Compatible device is the device itself. All the device may need to be IX-Compatible is to support sufficient internal communication to respond to the device requests of box 13. The physical medium of communication (whether wired or wireless) is unimportant, as any transport layer will suffice for carrying the messages for iExercise. In the preferred embodiment Multiple Devices/Multiple Users are handled at pre-initialization. If there are either multiple users or multiple devices, at initialization the activity is provided with data sufficient to allow the user to select who they are or what device they want. If the user is not found, default selection criteria are presented to allow a session without requiring the user to go through the user creation process. iExercise will save the training data in an "unassociated" slot with a user-defined tag for later recovery by the new user.

The preferred embodiment provides for three fundamental experience "styles". In the first style, the game provides an environment that provides a reasonably consistent intensity. Mountain bike trail, running race course—the activity leads, setting intensity based on the environment within a range defined by the training profile and user history. Rowing—constant intensity set by user. iExercise suggests initial intensity based on training profile and user history. Activity tailors intensity to reflect the model of the physical dynamics of the activity. Game environment—iExercise leads, providing callbacks when sets change. Game is free to make intensity settings based on the game environment within a given range specified by iExercise. The iExercise activity indicates what style it, or the user, wants at startup. iExercise responds with the initial settings and the device parameters.

Figure 14:
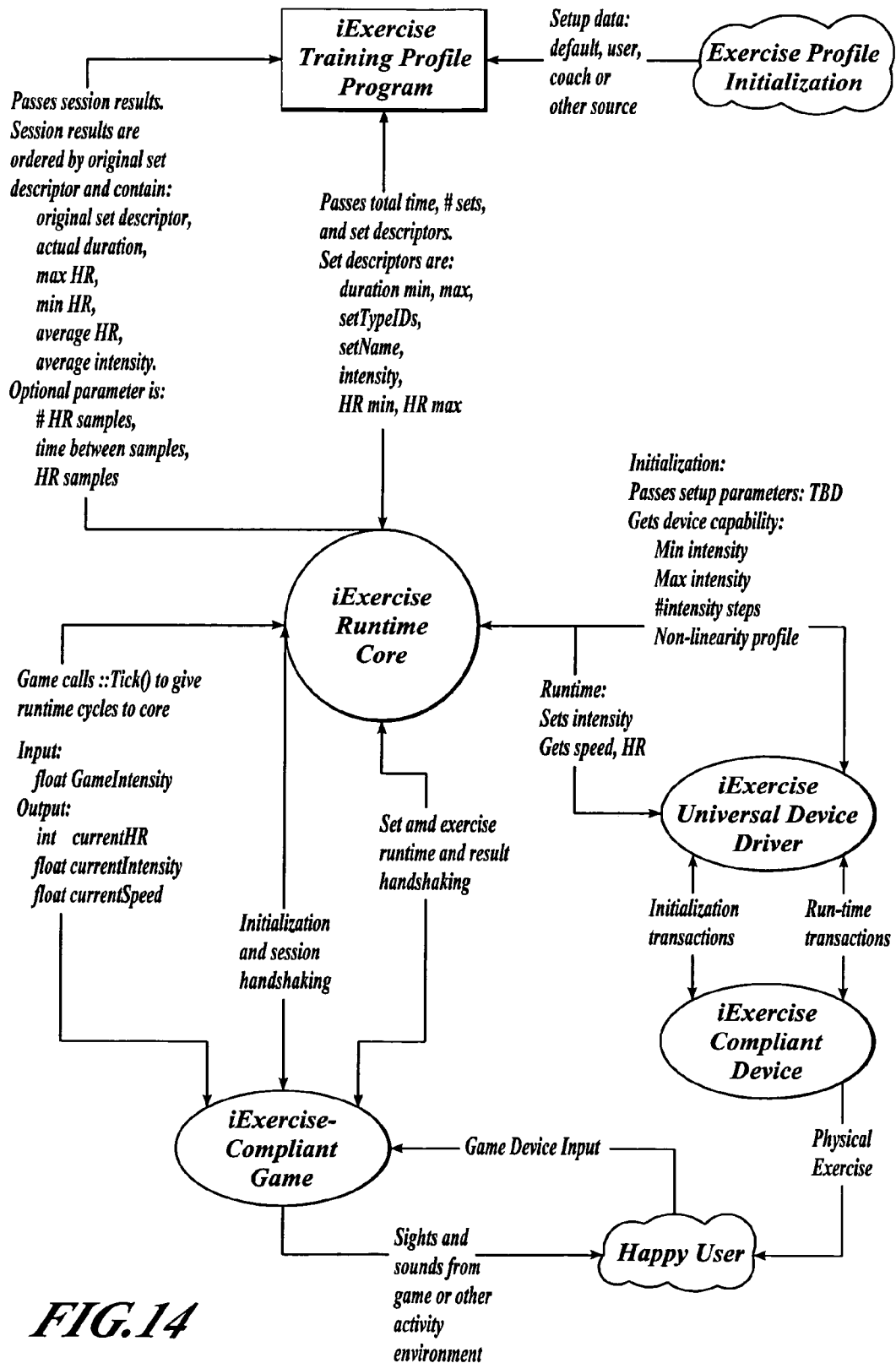
FIG. 14 shows that a preferred embodiment sets the standard for interactive exercise devices.

In the preferred embodiment Common Interactions with Runtime Core initialize in much the same way. The device descriptor is: Device Name: ASCII or Unicode character string; Device Type: iExercise-defined device type; and Device Capability: generic iExercise capabilities plus specific ones for device type. On Win32 platforms, the iExercise device driver will report as a DirectInput device and it is acceptable to deal with supplemental inputs (e.g., steering and brakes) through the DirectInput. This work has been done to allow devices with supplemental inputs to work directly as a joystick on all platforms, including Win32. FIG. 14 shows exercise profile initialization, training profile program, runtime core, the UDD and, more generally how the preferred embodiment sets the standard for interactive exercise devices. Explanation of the flowchart nodes or blocks are provided on the Figure itself.

Figure 15:
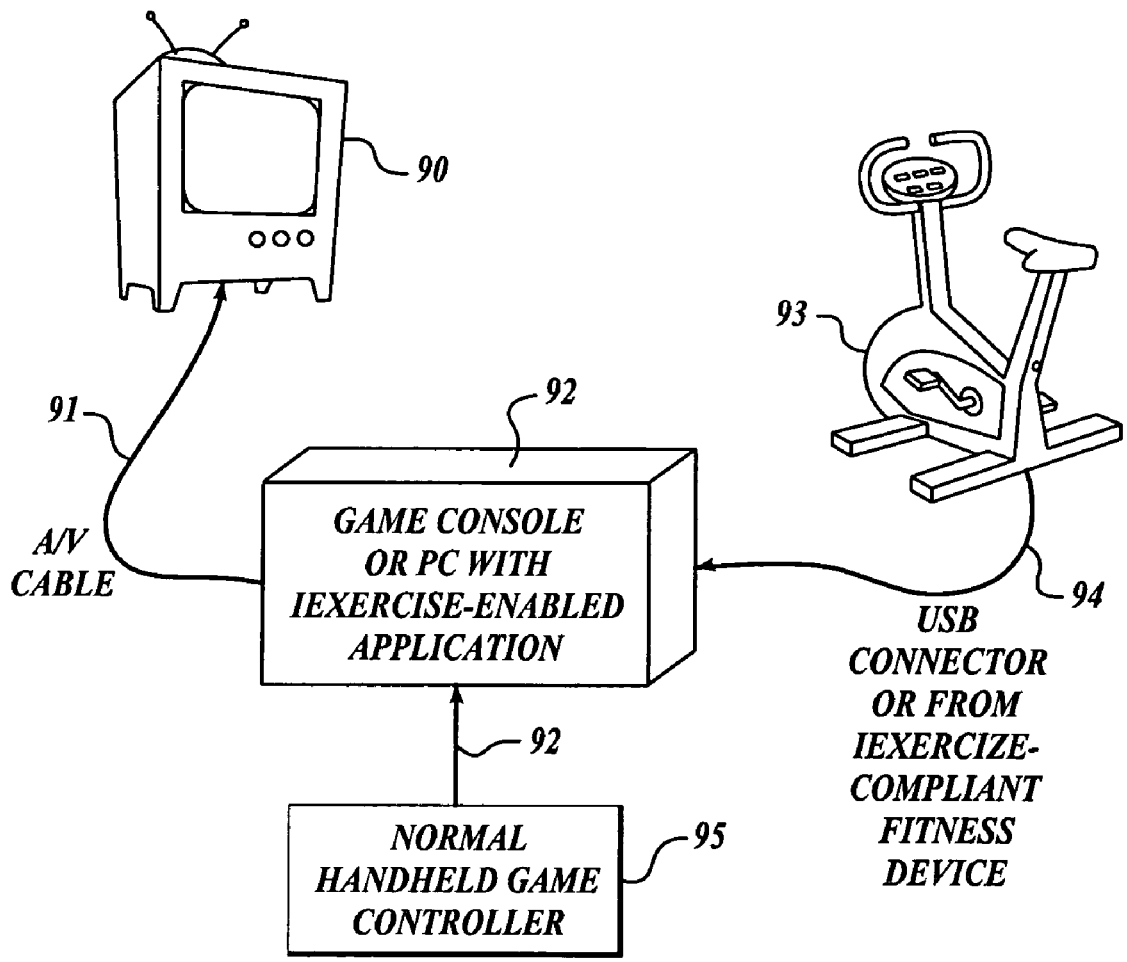
FIG. 15 shows fitness related equipment attached, in the preferred embodiment, to a game console or PC with an enabled application, which then may be connected via an AV cable to a television or other audio video device.
Figure 16:
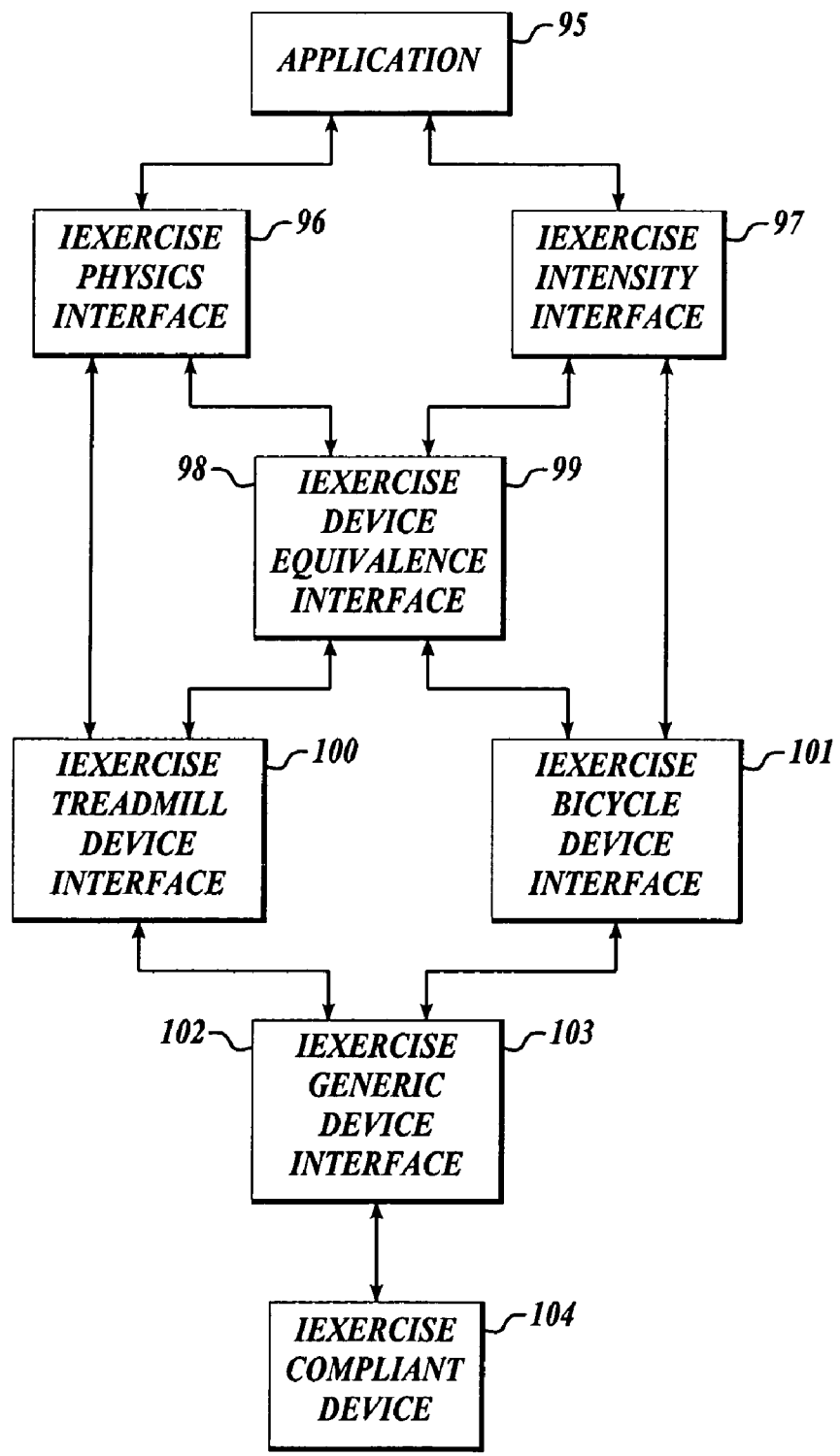
FIG. 16 shows a preferred embodiment's technical baseline.

FIG. 15 shows fitness related equipment 93 and 94 attached, in the preferred embodiment, to a game console or PC 92 with an iExercise enabled application, which then may be connected via an AV cable 91 to a television or other audio video device 90. FIG. 16 shows the preferred embodiment's technical baseline. IExercise can present any device as any other device, so applications can always get the device type they want. This means that every device can be used with every experience, it's one big market, not a bunch of little markets.

Figure 17:
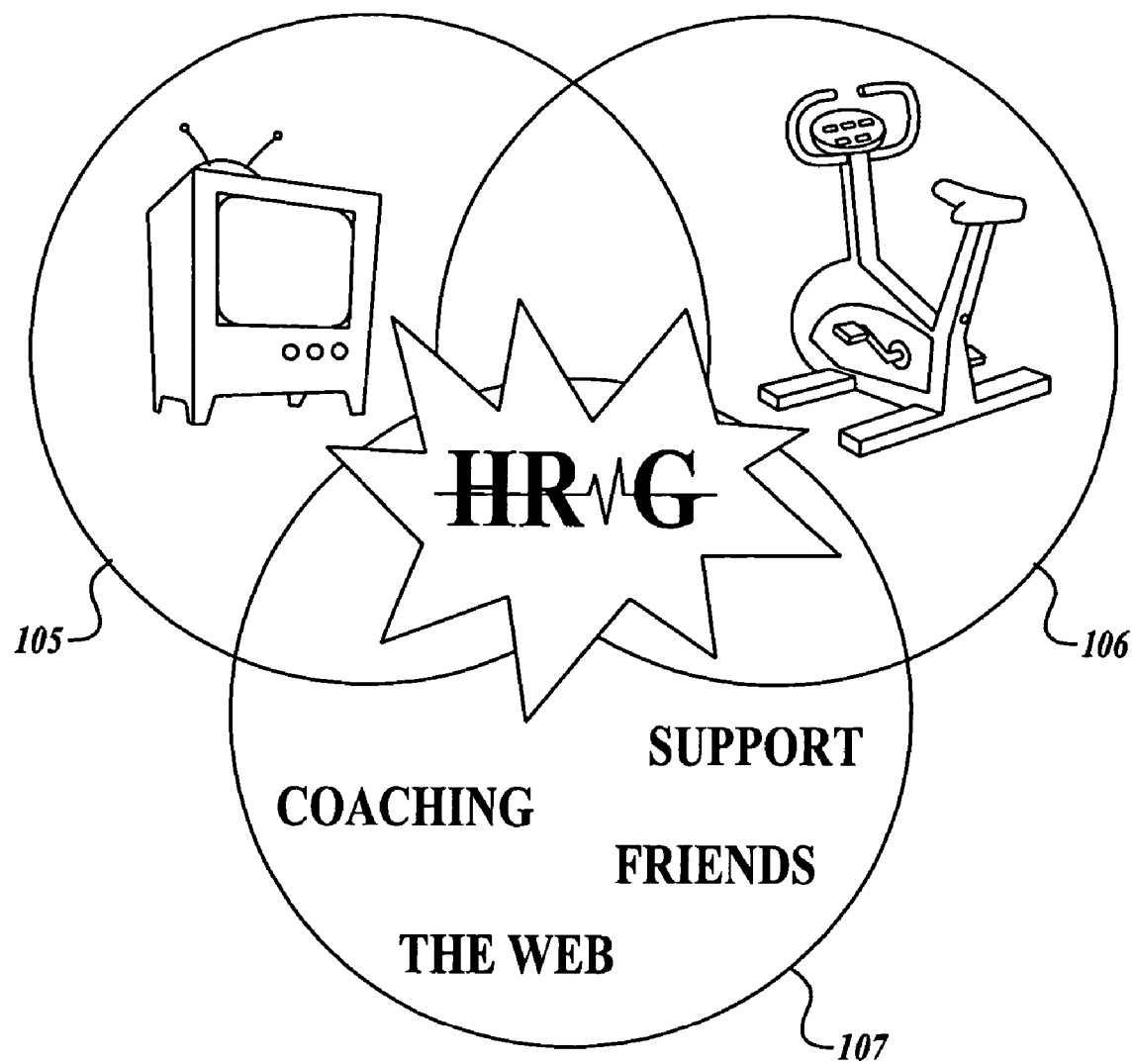
FIG. 17 shows how a preferred embodiment will include fitness, entertainment, and provide a user with many features and opportunities.

FIG. 17 shows how the preferred embodiment combines fitness 106, entertainment 105 and will provide a user with many features and opportunities 107. FIG. 18 is compares products 113 and features 112. The preferred embodiment is the only product that has all of the features as shown in the table. FIG. 19 is a table that shows the features 120 and that the preferred embodiment outperforms that product.

Figure 20:
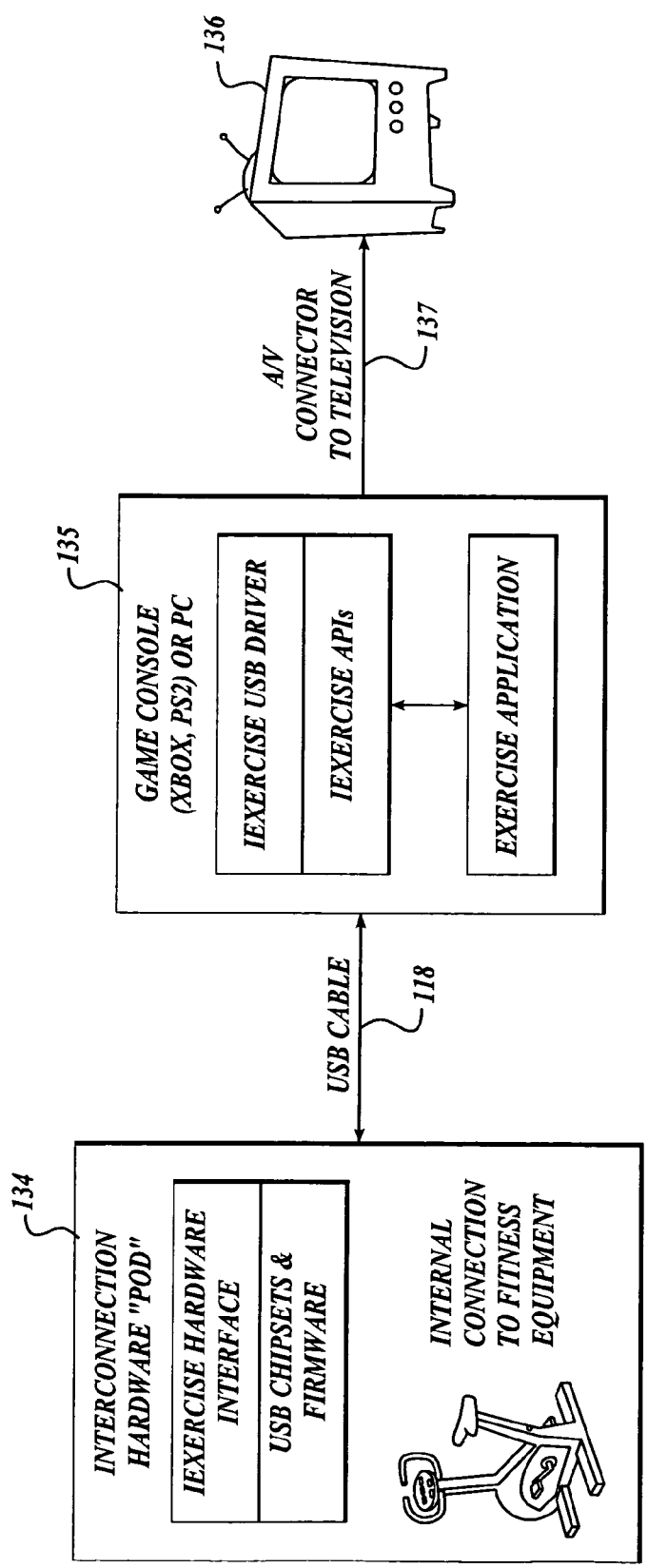
FIG. 20 shows a preferred platform and interconnectivity.

FIG. 20 shows the platform and interconnectivity of the preferred embodiment and shows a piece of fitness related equipment 134 attached 118, in the preferred embodiment, to a game console or PC 135 with an iExercise enabled application, which then may be connected via an AV cable 136 to a television or other AV device 137.

While the preferred and various alternate embodiments of the invention have been illustrated and described, as noted above, many changes can be made without departing from the spirit and scope of the invention. By way of example, and not limitation, while a USB interface is described for some embodiments, it should be understood that throughout the detailed description, any type of interface may be used without departing from the spirit of the invention. For example, Blue Tooth, FireWire, or any other custom or off the shelf type of interface. Similarly, any type of fitness or exercise equipment or computer hardware or software may be used, or any type of electronic game. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method for using a user interactive exercise system, the method comprising:
    activating at least one of an audio and video source communicatively connected with a computer system;
    running an application programming interface (API) by the computer system, the API compatible with a gaming code including chirpmaker code, HRG code, and universal serial bus code;

capturing data from the at least one of an audio and video source;

transmitting the data to at least one exercise apparatus;

coordinating an exercise program written in the gaming code that is synchronized with at least one of the audio and video source, the exercise program having user-engagable images; and modifying the plurality of user-engagable images using the gaming code configured to adjust for at least one of a user calibrated level of effort of a same type exercise apparatus, a user calibrated level of effort of a dissimilar type exercise apparatus, a user experience level with the exercise apparatus, a user weight, a user weight shift while operating the at least one apparatus, a user heart rate, a user fitness level, a user exercise plan, a change in the user's exercise plan from determination of the user's fitness level, a user's output energy, the exercise apparatus power characteristic, and a simulated workout resistance.

2. The method of claim 1, wherein capturing data includes capturing data from a previously created exercise program.

* * * * *